(12) United States Patent
Unger

(10) Patent No.: US 9,650,244 B2
(45) Date of Patent: May 16, 2017

(54) TOPICAL VACCINATION VIA DNA MICROPARTICLES

(75) Inventor: Gretchen Unger, Chaska, MN (US)

(73) Assignee: Genesegues, Inc., Chaska, MN (US)

( * ) Notice: Subject to any disclaimer, the term of this patent is extended or adjusted under 35 U.S.C. 154(b) by 0 days.

(21) Appl. No.: 13/218,165

(22) Filed: Aug. 25, 2011

(65) Prior Publication Data

US 2012/0225125 A1    Sep. 6, 2012

Related U.S. Application Data

(63) Continuation-in-part of application No. 13/071,067, filed on Mar. 24, 2011, now abandoned.

(60) Provisional application No. 61/402,202, filed on Aug. 25, 2010, provisional application No. 61/403,491, filed on Sep. 15, 2010.

(51) Int. Cl.
| | | |
|---|---|---|
| *A61K 39/395* | (2006.01) |
| *B82Y 5/00* | (2011.01) |
| *A61K 9/51* | (2006.01) |
| *A61K 31/713* | (2006.01) |
| *A61K 39/00* | (2006.01) |

(52) U.S. Cl.
CPC .............. *B82Y 5/00* (2013.01); *A61K 9/5115* (2013.01); *A61K 9/5123* (2013.01); *A61K 9/5161* (2013.01); *A61K 31/713* (2013.01); *A61K 2039/55505* (2013.01); *A61K 2039/55555* (2013.01)

(58) Field of Classification Search
None
See application file for complete search history.

(56) References Cited

U.S. PATENT DOCUMENTS

| 6,593,308 B2 * | 7/2003 | Szoka, Jr. ........................ 514/54 |
| 6,632,671 B2 | 10/2003 | Unger |
| 7,465,716 B2 | 12/2008 | Szoka, Jr. |
| 2007/0098713 A1 | 5/2007 | Unger |

OTHER PUBLICATIONS

Babiuk, et al. (2000) Journal of Controlled Release, 66:199-214, "Cutaneous vaccination the skin as an immunologically active tissue and the challenge of antigen delivery".
Barfoed, et al. (2004) Vaccine 22:1395-1405, "Influence of routes and administration parameters on antibody response of pigs following DNA vaccination".
Chen, et al. (2009) Journal of Controlled Release 139:212-220, "Dry-coated microprojection array patches for targeted delivery of immunotherapeutics to the skin".
Choi, et al. (2006) Current Drug Delivery 3:37-45, "Topical DNA vaccination with DNA/Lipid based complex".
Companjen, et al. (2001) Archives of Dermatological Research 293:184-190, "A modified ex vivo skin organ culture system for functional studies".
Dean, et al. (2005) Expert Opinion Drug Delivery 2(2):227-236, "Epidermal delivery of protein and DNA vaccines".
Do, et al. (2004) Journal of Immunotherapy 27(1):1-12, "Role of CD44 and Hyaluronic Acid (HA) in Activation of Alloreactive and Antigen-Specific T Cells by Bone Marrow-Derived Dendritic Cells".
Fischer, et al. (2010) Bioconjugate Chemistry 21(6):1018-1022, "Conjugation to nickel-chelating nanolipoprotein particles increases the potency and efficacy of subunit vaccines to prevent West Nile encephalitis".
Foldvari, et al. (2010) Molecular Pharmaceutics 7(3):751-762, "Topical evidence of interpheron alpha by biphasic vesicles Evidence for a novel nanopathway across the stratum corneum".
Gerdts, et al. (2007) Future Microbiology 2(6):667-675, "Use of animal models in the development of human vaccines".
Hein, et al. (2002) Nature Reviews Immunology 3:79-85, "A road less travelled large animal models in immunological research".
Hengge (2006) Gene Therapy 13:1555-1563, "Gene therapy progress and prospect the skin—easily accessible, but still far away".
Hirao (2008) Vaccine 26:440-448, "Intradermal/subcutaneous immunization by electroporation improves plasmid vaccine delivery and potency in pigs and rhesus monkeys".
Huang (2007) Seminars in Immunopathology 29:71-80, "Topical vaccination the skin as a unique portal to adaptive immune responses".
Ishii, et al. (2001) Journal of Investigative Dermatology Symprosium Proceedings 6(1):76-80, "Immunologic Characterization of HIV-specific DNA vaccine".
Iwasaki, et al. (2010) Science 327:291-295, "Regulation of adaptive immunity by the innate immune system".
Lesley, et al. (2000) Journal of Biological Chemistry 275(35):26967-26975, "Hyaluronan binding by cell surface CD44".
Liszewicz, et al. (2004) Journal of Investigative Dermatology 124(1):160-169, "Dermavir a novel topical vaccine for HIV/AIDS".
Mahe, et al. (2009) Journal of Investigative Dermatology 129:1156-1164, "Nanoparticle-based targeting of vaccine compounds to skin antigen-presenting cells by hair follicles and their transport in mice".
Pilling, et al. (2002) Toxicologic Pathway 30(3):298-305, "The assessment of local tolerance, acute toxicity, and DNA biodistribution following particle-mediate delivery of a DNA vaccine to minipigs".
Powell and Horton (2005) Immunologic Research 32(1):207-218, "Threat matrix Low-molecular-weight hyaluronan (HA) as a danger signal".
Swindle (2008) Technical Bulletin, Sinclair Research, pp. 1-4, "Porcine integumentary system models: Part 1—Dermal toxicology".
Termeer, et al. (2001) Journal of Leukocyte Biology 70:715-722, "The role of CD44 during CD40 ligand-induced dendritic cell clustering and migration".
Unger (2004) SBIR Website Abstract [Online] p. 1, "s50 nanocapsules for transcutaneous DNA vaccination"; Available Web Site: http://www.sbir.gov/sbirsearch/detail/173406 Last update: unknown; Accessed on: Sep. 10, 2011.

(Continued)

*Primary Examiner* — Yunsoo Kim
(74) *Attorney, Agent, or Firm* — Swanson & Bratschun, L.L.C.

(57) ABSTRACT

Disclosed are drug delivery systems and methods for extravascular administration of drug, vaccine, and/or diagnostic agents, for use in research and medical applications.

12 Claims, 8 Drawing Sheets

(56) References Cited

OTHER PUBLICATIONS

Figure 1:
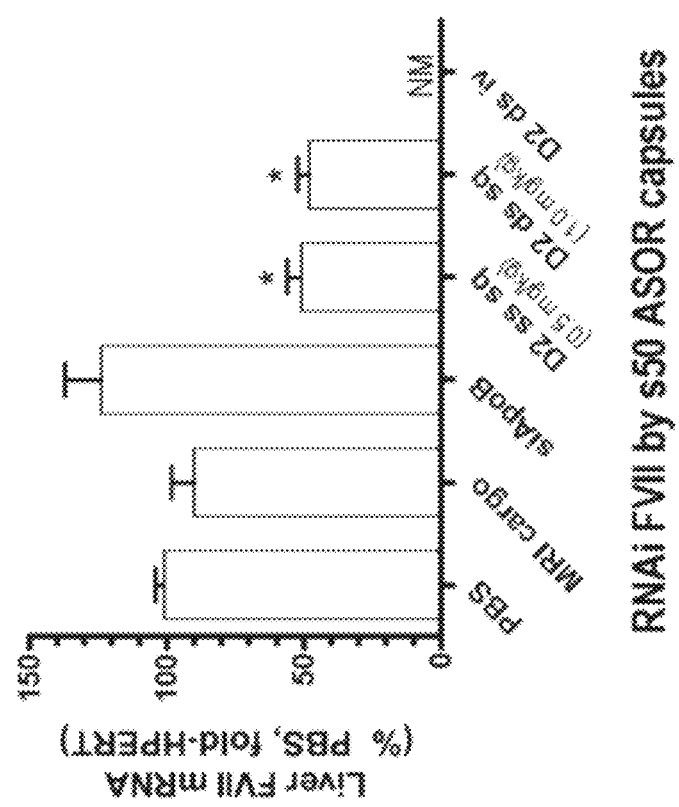
Figures 2A, 2B:
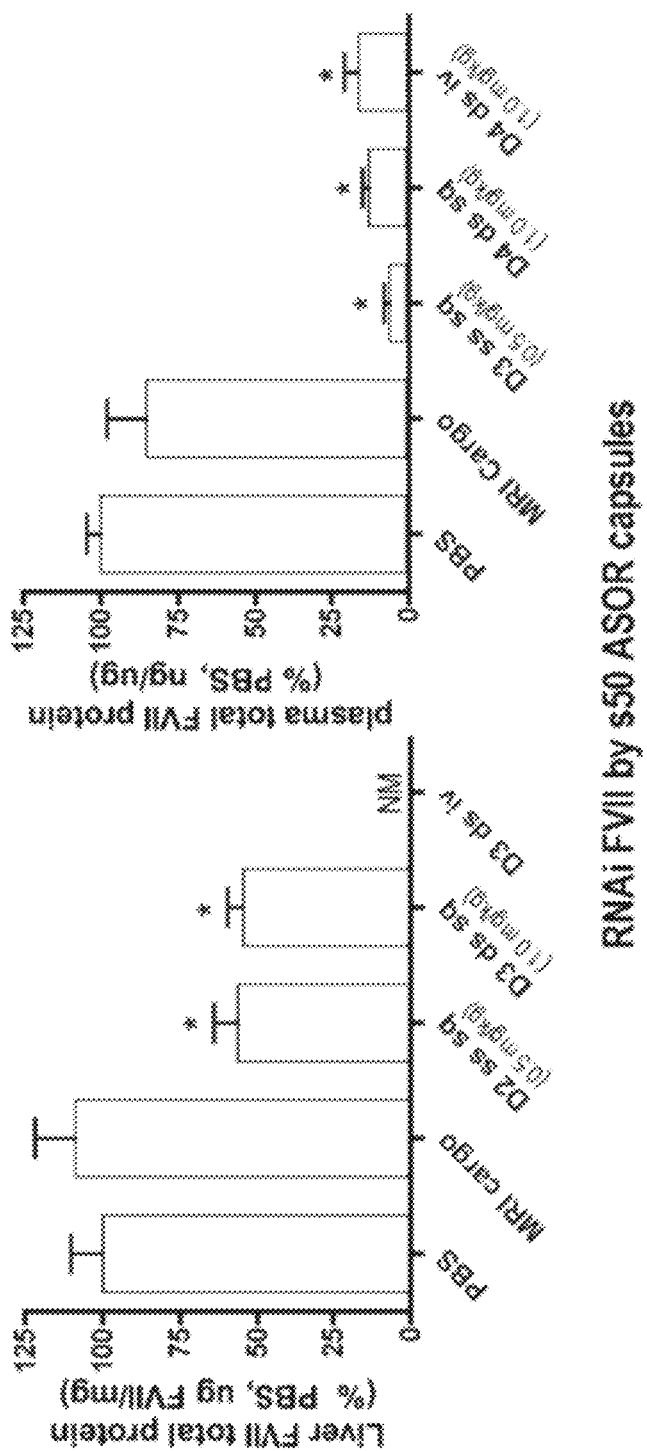

Vogt, et al. (2006) Journal of Investigative Dermatology 126:1316-1322, "40 nm, but not 750 or 1,500 nm, nanoparticles enter epidermal CD1a +cells after transcutaneous application on skin".

Yan, et al. (2009) HIV/AIDS—Research and Palliative Care 1:1-11, "Lipid nanoparticles with accessible nickel as a vaccine delivery system for single and multiple HIS-tagged HIV antigens".

Mizrahy, et al. (2011) Journal of Controlled Release 156:231-238, "Hyaluronan-coated nanoparticles: The influence of the molecular weight on CD44-hyaluronan interactions and on the immune response".

Scheibner, et al. (2006) Journal of Immunology 177:1272-1281, "Hyaluronan Fragments Act as an Endogenous Danger Signal by Engaging TLR2".

Ghosh, et al., 1997, "Transdermal and Topical Drug Delivery Systems" Interpharm Press, Inc., Buffalo Grove, Illinois (pp. 46-49 and 156-157 and 200-201).

\* cited by examiner

TOPICAL VACCINATION VIA DNA MICROPARTICLES

RELATED APPLICATIONS AND INCORPORATIONS BY REFERENCE

This application is a Continuation-in-Part of U.S. patent application Ser. No. 13/071,067, filed Mar. 24, 2011 now abandoned and claims priority to U.S. Provisional Patent Application No. 61/402,202, filed Aug. 25, 2010, and 61/403,491, filed Sep. 15, 2010, each of which is incorporated herein by reference in its entirety.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

STATEMENT REGARDING GOVERNMENT RIGHTS

The U.S. Government may have certain rights in this application pursuant to Grant Nos. 1R43DK084644-01 and 1R43AI06268-01 and Contract No. HHSN261200800027C awarded by the National Institutes of Health.

TECHNICAL FIELD

The invention relates to compositions for and methods of treating, diagnosing, and/or vaccinating a subject comprising extravascularly administering nanoparticles comprising a drug, vaccine, and/or diagnostic agent.

BACKGROUND

Many drugs and vaccines are administered intravenously, so that the agent is directly available in the bloodstream and reaches its intended site at a significant concentration. The chief obstacle to treatment strategies involving macromolecules is their generally poor bioavailability, resulting in either ineffective treatment or in high dosages that significantly limit their therapeutic applications due to cost.

SUMMARY OF THE INVENTION

It would be advantageous if therapeutic agents, including vaccines, and diagnostic agents could be efficaciously administered using methods that are easier to handle for the subject and/or are amenable to repeat dosing. For example, subcutaneous administration does not require venous access, can often be self-administered, and typically requires a smaller needle size. Topical administration is minimally invasive or non-invasive, can be self-administered, and, with regard to vaccine applications, provides more direct access to the highly specialized immune system located in the skin.

In one embodiment, the invention provides a non-viral drug delivery system and in another, a method for improved delivery of cargo, including therapeutics, vaccines, and imaging agents, by non-intravenous administration. It has been found that non-intravenous administration of low dosages of targeted nanoparticles results in target modulation equivalent or superior to that resulting upon intravenous administration. These unexpected results allow for advantages, compared to intravenous administration, which include greater convenience (patients can be treated at home or in a physician's office, rather than at hospitals or infusion centers), increased compliance, reduced treatment cost, and more efficient use of healthcare resources.

Disclosed herein are compositions and methods that demonstrate the flexibility of nanoparticles to successfully accommodate ligands and cargoes of choice, for extravascular, including subcutaneous and topical, delivery. There are several diseases and classes of drugs for which the availability of targeted nanoparticles for extravascular delivery would enhance treatment and diagnostic options. For example, the class of drugs known as RNA interference (RNAi) agents holds the potential to make any gene into a drug target, a significant advance over conventional therapies that can target only a relatively small portion of the genome. However, despite tremendously broad interest and investment in RNAi, there are currently no subcutaneous applications of the same in the clinic.

Delivery modes for RNAi-based therapies in the clinic can be characterized as either intravenous (e.g., Alnylam's ALN-VSP for treatment of liver cancers and solid tumors; Calando's CALAA-01 for solid tumors; Quark's 15NP for acute kidney injuries; Silence Therapeutics' Atu027/Atu093 for lung cancers; and Tekmira's liposomal treatment for hypercholesterolemia) or local (e.g., Alnylam's intranasal RSV-P for respiratory syncytial virus; Duke University's intradermal treatment using siRNA-transfected dendritic cells to treat melanoma; and Sylentis' intraocular treatment for glaucoma).

Disclosed herein are nanoparticle compositions bearing drug, vaccine, and/or diagnostic agents, methods for synthesis, and methods for extravascular administration and use in research and medical applications. The disclosed compositions include a nanoparticle comprising a core comprised of drug, vaccine, and/or diagnostic agent; a surfactant substantially surrounding the core to form a surfactant-coated complex, wherein the surfactant has an HLB value of less than about 6.0 units; and a shell that non-covalently adheres to and substantially surrounds the surfactant-coated complex, wherein the shell comprises a targeting moiety and a cationic precipitating agent comprising lithium. The mean diameter of the resulting nanoparticle is less than about 50 nanometers.

Additionally disclosed are methods for synthesizing the nanoparticles described herein, including introducing into an aqueous composition a plurality of drug, vaccine, and/or diagnostic agents to create a core mixture, disposing into the core mixture a hydrophobic surfactant to create a surfactant complex mixture, wherein the hydrophobic surfactant has an HLB value of less than about 6.0 units, and mixing the surfactant complex mixture with a precipitating solution comprising a targeting moiety and a cationic precipitating agent comprised of lithium to create a precipitated nanoparticle mixture, resulting in nanoparticles comprising the therapeutic or diagnostic core substantially surrounded by the hydrophobic surfactant, which is substantially surrounded by the targeting moiety and cationic precipitating agent.

The disclosed nanoparticles provide specific targeting and intact delivery of cargo in an efficient composition. In one embodiment, the therapeutic cargo comprises more than about two-thirds of the total weight of the nanoparticle. In addition, the disclosed nanoparticles are compatible with a range of drug, vaccine, and diagnostic cargoes. Furthermore, the disclosed nanoparticles provide a modular targeting component that can be readily synthesized for a given cellular target, without the steps of chelating, conjugating, or covalently attaching the targeting moiety to the nanoparticle. With judicious selection of targeting moiety and/or particle size, the nanoparticles are capable of delivering cargo to targeted tissue and cells of the epidermis, dermis, or subcutaneous tissues, or muscle, or to other targeted tissue and cells reached via the lymph nodes or the systemic circulation.

In another embodiment, the invention provides methods of treatment comprising administering to a subject in need thereof a therapeutically effective amount of a formulated composition according to the invention, including via extravascular, for example, subcutaneous and/or topical, administration.

In one embodiment, the invention provides a method of treating a disease or disorder, comprising administering to a subject in need of such treatment, a therapeutically effective amount of non-viral nanoparticles, wherein said nanoparticles comprise a micelle core comprising a bioactive macromolecule and a surfactant with an HLB value of less than or equal to about 6.0, a shell adsorbed to the micelle core and comprising a ligand and lithium, and having a mean diameter of less than about 50 nanometers, wherein; (a) the bioactive macromolecule comprises an oligonucleotide, a protein, a peptide, a carbohydrate, or an antibody; (b) the ligand comprises a protein, a peptide, a carbohydrate, an antibody, or a small molecule; and (c) the nanoparticles are administered subcutaneously.

In another embodiment, the bioactive macromolecule comprises an oligonucleotide or a therapeutic plasmid. In still another embodiment, the bioactive macromolecule comprises an oligonucleotide, and the dose administered of the oligonucleotide is less than or equal to about 5 mg/kg. In another embodiment, the ligand is Asialoorosomucoid (ASOR).

In another embodiment, the bioactive macromolecule comprises a therapeutic plasmid, and the administering comprises repeat dosing. In still another embodiment, the bioactive macromolecule comprises a therapeutic plasmid, and the dose administered of the plasmid is greater than or equal to about 10 mg/kg.

In one embodiment, the invention provides a pharmaceutical composition comprising non-viral nanoparticles comprising a micelle core comprising an antigen and a surfactant with an HLB value of less than or equal to about 6.0, a shell adsorbed to the micelle core and comprising a ligand, lithium, and an adjuvant, and having a mean diameter of less than about 50 nanometers, wherein; (a) the antigen is hydrophilic and comprises a DNA plasmid, a protein, or a peptide; (b) the adjuvant comprises nickel; and (c) the ligand comprises hyaluronan, wherein said hyaluronan ligand has an average molecular weight of less than about 50,000 Daltons and is non-covalently attached to the nanoparticles. In other embodiments, the ligand is fibronectin, alpha V betaV, antiCV44, or antiDec205. In still other embodiments, the ligand is a molecule such as a carbohydrate, protein, peptide, or antibody that targets receptors of both keratinocytes and dendritic cells.

It has been discovered that topically delivering nickel-adjuvanted antigen in the inventive particles targeted to both keratinocytes and dendritic cells generates improved and more persistent mucosal IgA response over the formula targeted to dendritic cells only. This is surprising because the view in the art is that keratinocyte cells are only weakly immunogenic, and that any antigen delivered to keratinocytes diverts from the more immunogenic dendritic cells.

In another embodiment, the invention provides a method of inducing an immune response in a subject, comprising administering to the subject an effective amount of the composition, wherein the composition is topically administered.

In one embodiment, the invention provides a composition for imaging a subject, said composition comprising non-viral nanoparticles comprising a micelle core comprising an imaging agent, wherein the imaging agent is dysprosium, and a surfactant with an HLB value of less than or equal to about 6.0, a shell adsorbed to the micelle core and comprising a ligand and lithium, and having a mean diameter of less than about 50 nanometers. In another embodiment, the dysprosium is chelated to a DOTA-Dextran conjugate. In still another embodiment, the subject is a human.

The foregoing has outlined rather broadly some of the embodiments of the invention in order that the detailed description of the invention that follows may be better understood. Other aspects of the invention are described in or are obvious from the following disclosure and are within the ambit of the invention.

The terms "nanocapsule" and "nanoparticle" are used interchangeably herein.

Unless otherwise defined, all technical and scientific terms used herein have the same meaning as is commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples described herein are illustrative only and are not intended to be limiting.

BRIEF DESCRIPTION OF THE DRAWINGS

The following Detailed Description of the Invention, given by way of Examples, but not intended to limit the invention to specific embodiments described, may be understood in conjunction with the accompanying figures, in which:

FIG. 1 shows a bar graph depicting the knockdown of Factor VII (FVII) mRNA in mouse liver after a single treatment with asialoorosomucoid (ASOR)-coated sub-50 nanometer (s50) capsules bearing single- and double-stranded RNAi cargo. "D#" indicates number of days after treatment. "ss" indicates FVII single-stranded oligonucleotide. "ds" indicates FVII double-stranded siRNA. "sq" indicates subcutaneous administration. "iv" indicates intravenous administration. "NM" means not measured. There were n=5-13 animals per group.

FIGS. 2A and 2B show bar graphs depicting the reduction of FVII total protein in mouse liver (2A) and plasma (2B) after a single treatment with ASOR-coated s50 capsules bearing single- and double-stranded RNAi cargo. "D#" indicates number of days after treatment. "ss" indicates FVII single-stranded oligonucleotide. "ds" indicates FVII double-stranded siRNA. "sq" indicates subcutaneous administration. "iv" indicates intravenous administration. "NM" means not measured. There were n=3-8 animals per group.

Figures 3A, 3B:
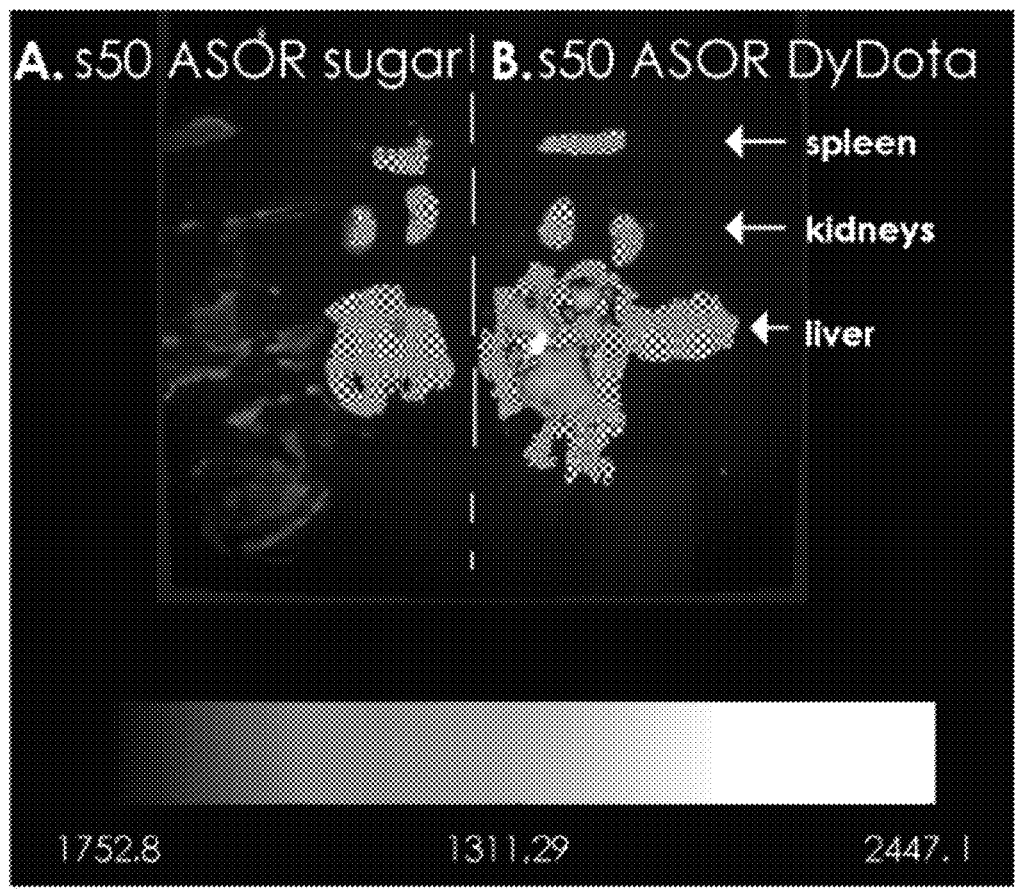

FIGS. 3A and 3B depict near infrared (NIR) imaging with ASOR coated s50 particles bearing DyDex cargo, demonstrating capability of s50 DyDex as an imaging agent to elucidate the specific sites of capsule delivery. Mice were intravenously injected (right-side of FIG. 3B) or not (left-side of FIG. 3A) with 100 nmol/kg of s50 ASOR DyDex about 30 hours before imaging. Excised livers, kidneys, or spleen were imaged on at Kodak Carestream FX pro imaging station at 510 excitation and 700 nm emission. Results were processed with Kodak Multispectral imaging analysis software to extract Dy-specific signal. The checkerboard pattern denotes green background signal (i.e. no Dy detection) in the original pseudocolored data. Gray-to-white signal in liver denotes increasing Dy concentration; a numerical representation of intensity is illustrated in the calibration scale at the lower edge of the figure.

Figure 4:
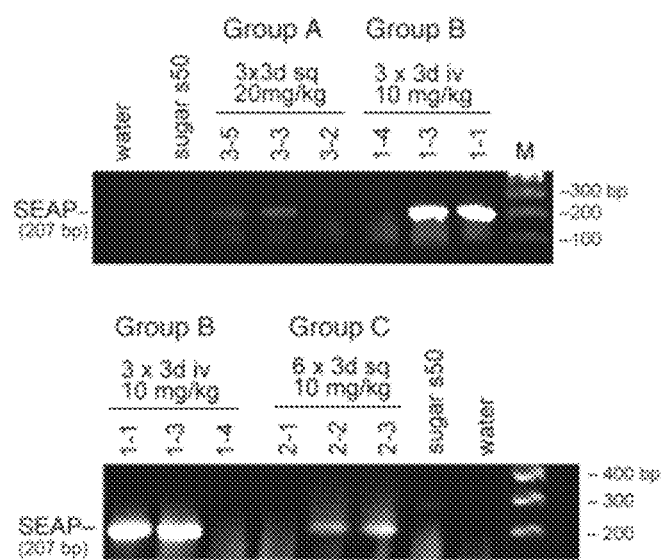

FIG. 4 shows two gels demonstrating hepatocyte-targeted subcutaneous (sq) delivery of ASOR-coated s50 capsules bearing plasmid DNA in mice. SEAP-specific polymerase chain reaction (PCR) products are visualized by electrophoresis on 1.25% agarose gels using ethidium bromide. Input for the reactions was reverse transcriptase product from total RNA isolated from animals treated with ASOR sugar (3×10 mg/kg q3D intravenous) and ASOR pCpGMarSEAP using different regimens: Group A=3×20 mg/kg q3 Day sq, Group C=6×10 mg/kg q3 Day sq, and comparator Group B=3×10 mg/kg q3 Day intravenously. There were n=3 animals per treatment group. Tissue was collected two days after the last dose.

Figure 5:
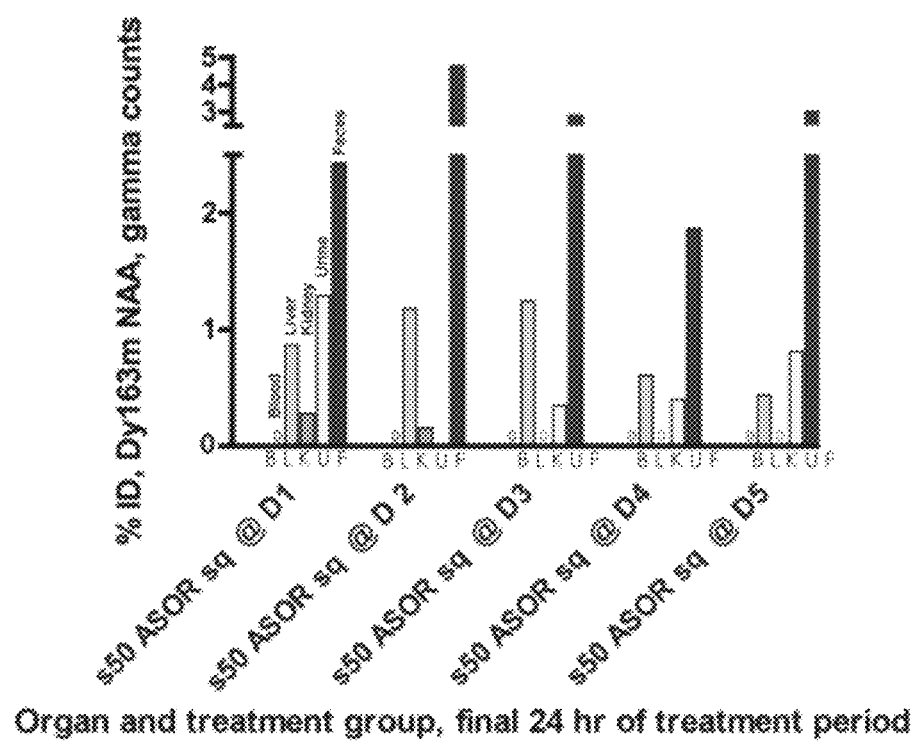

FIG. 5 shows a bar graph depicting site accumulation of s50 subcutaneously-delivered DyDex cargo targeted to liver in mice over a 5-day period, demonstrating liver targeting specificity and prolonged availability of the cargo. Mice were treated sq with ASOR-ligand, s50 capsules having a mean diameter of 10-12 nanometers and bearing Dy-labeled Dextran at 100 nmol Dy/kg for sensitive Dy-163 m neutron activation analysis (NAA) of tissues. Tissues were collected daily for five days (n=1 mouse per 24 hour timepoint). Mice were housed in metabolism cages for urine and feces collection for the last 24 hours of the respective treatment periods. Tissues were weighed and neutron irradiated in a fusion reactor facility for gamma counting of metastable Dy-163 spectra.

Figure 6A:
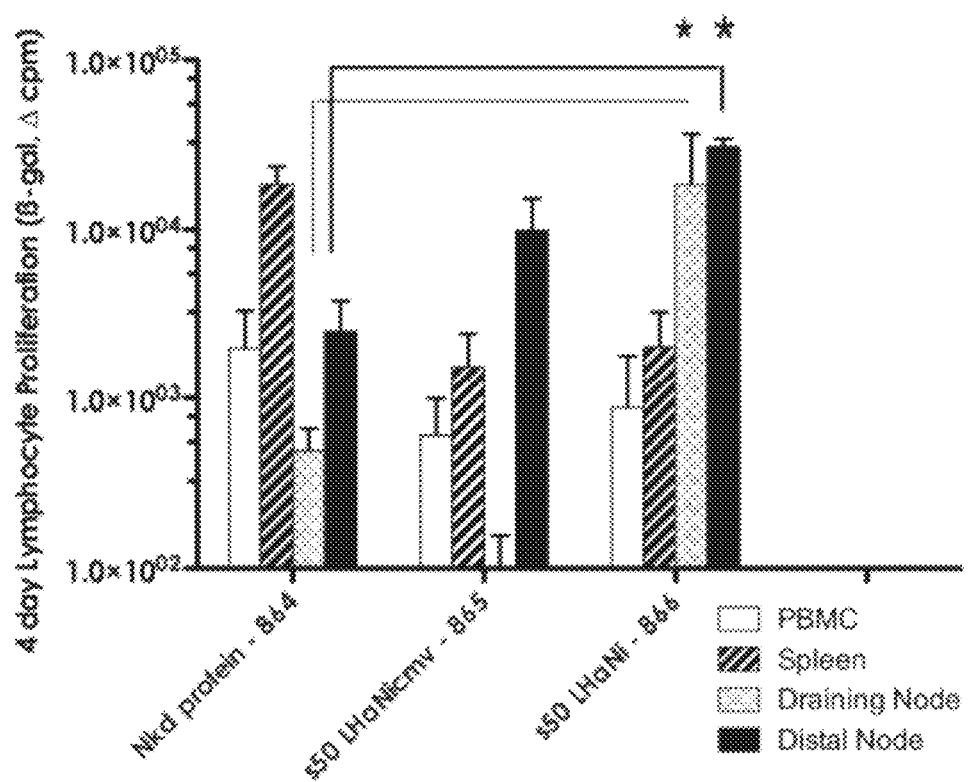

FIG. 6A shows a bar graph displaying 4-day lymphoproliferation responses from lymphocyte cultures to challenge by 50 μg/ml of recombinant bacterial betagalactosidase. Lymphocytes were either peripheral blood monocyte cells or isolated from spleen, draining lymph nodes (mandibular), or distal lymph nodes (pubescent) from week 7 terminal samples. For quantitation, 0.5 μcurie of tritium was added to cultures during the last eighteen hours of culture to measure ongoing DNA synthesis and, thus, proliferation.

Figure 6B:
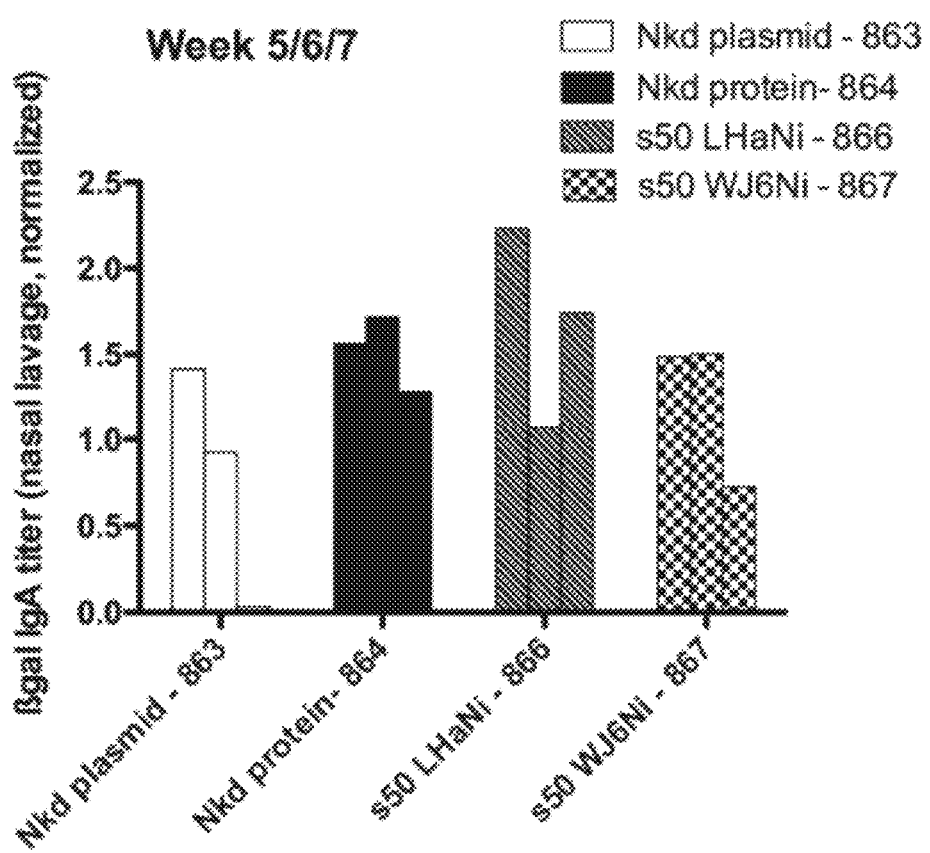

FIG. 6B shows a bar graph displaying antigen-specific mucosal IgA antibodies assayed in nasal lavage by Bgal ELISA and normalized by lavage protein concentration. Nasal lavage was collected from pigs under light isofluorane anesthesia by injecting 10 mL PBS up one nostril using a catheter as a syringe and collecting outflow from the other nostril via a funnel. Samples were collected for the last three weeks of the study. Very low levels of normalized IgA antibodies were measured in week 7 lavage from pig #863 receiving intradermal naked plasmid, providing an estimate of background levels.

Figure 6C:
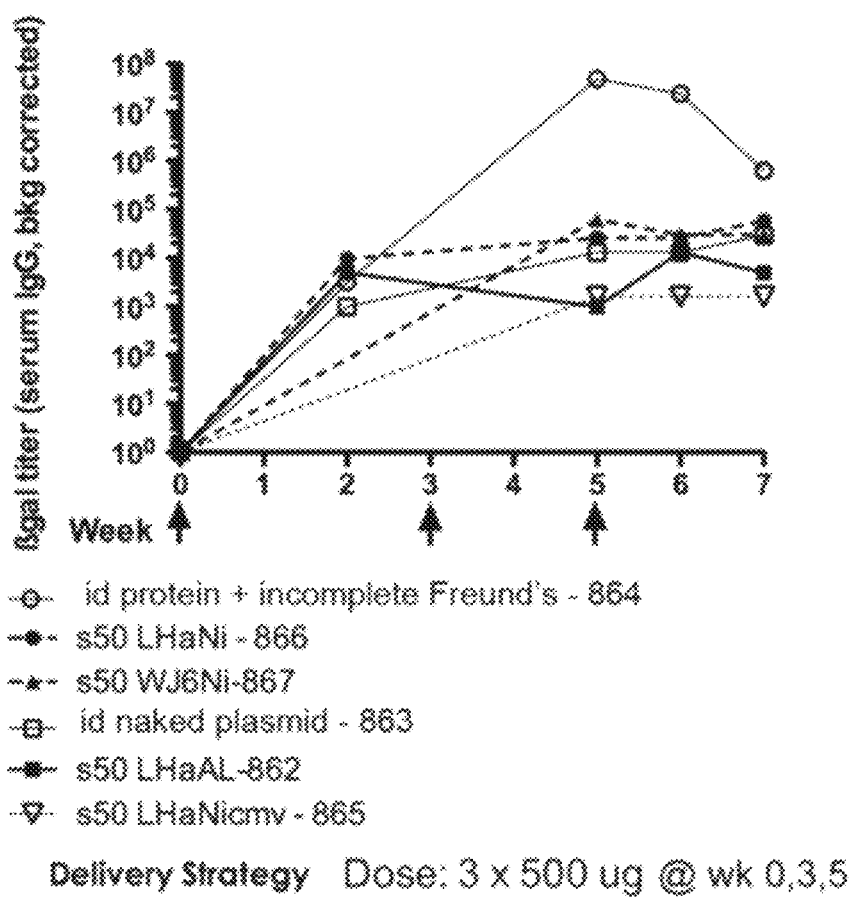

FIG. 6C shows a line graph depicting the development of serum IgG antibodies against Bgal generated by ELISA. Background from pre-immune serum is subtracted. Arrows denote treatment schedule; sera were collected at weeks 2, 5, 6, and terminal week 7.

DETAILED DESCRIPTION OF THE INVENTION

Definitions

The term "subject", as used herein, refers to a mammal. In separate additional embodiments, the subject is a human or a veterinary mammal. In the context of the vaccination/immune response induction compositions and methods, in one embodiment, the subject is a large mammal; in another embodiment, the subject is a non-rodent mammal; in another embodiment, the subject is a veterinary mammal; in another embodiment, the subject is a swine; in another embodiment, the subject is a human; in another embodiment, the subject weighs more than about five pounds. In the context of imaging/diagnostic methods disclosed herein, the "subject" includes, without limitation, a cell, a tissue, an organ, and/or a mammal.

The term "extravascular", as used herein, refers to non-oral methods of administration excluding intravenous methods. It includes, without limitation, subcutaneous, topical, intramuscular, intradermal, transdermal, transcutaneous, transmucosal, and intracerebral administration.

The terms "comprises", "comprising", are intended to have the broad meaning ascribed to them in U.S. Patent Law and can mean "includes", "including" and the like. Moreover, the use of the term "including", as well as other forms, such as "includes" and "included", is not limiting.

The invention can be understood more fully by reference to the following detailed description and illustrative examples, which are intended to exemplify non-limiting embodiments of the invention.

Additional Embodiments of the Invention

In some embodiments, the nanoparticles described herein comprise a core comprising a therapeutic or diagnostic agent; a surfactant substantially surrounding the core to form a surfactant-coated complex, wherein the surfactant has an HLB value of less than about 6.0 units; and a shell that non-covalently adheres to and substantially surrounds the surfactant-coated complex, wherein the shell comprises a targeting moiety and lithium. The mean diameter of the resulting nanoparticle is less than about 50 nanometers (sub-50 nanometer capsules, "s50 capsules").

In a further embodiment of the invention, the mean size of the nanoparticle is less than about 50 nanometers in diameter, as measured by atomic force microscopy after drying of the nanoparticles. In still a further embodiment of the invention, the mean size of the nanoparticle is less than about 40 nanometers. In still a further embodiment of the invention, the mean size of the nanoparticle is less than about 30 nanometers. In still a further embodiment of the invention, the mean size of the nanoparticle is less than about 20 nanometers. In still a further embodiment of the invention, the mean size of the nanoparticle is less than about 10 nanometers. In still a further embodiment of the invention, the mean size of the nanoparticle is no less than about 8 nanometers. In still a further embodiment of the invention, the mean size of the nanoparticle is no less than about 5 nanometers. In yet another embodiment of the invention, the mean size of the nanoparticle is between about 5 and about 50 nanometers.

In additional embodiments comprising subcutaneous administration of oligonucleotides, the mean diameter of the nanoparticles is less than or equal to about 25 nm, less than or equal to about 22 nm, between about 20 and about 25 nm, or between about 10 and about 25 nm. Nanoparticle diameter is determined as the mean of the minor and major particle axis of a dried-down particle (for example, dried down on a mica sheet), and obtained by atomic force microscopy, in one embodiment, using ImageJ software.

In one embodiment of the invention, the core of the nanoparticle comprises a drug/therapeutic agent, a vaccine agent, or a diagnostic agent or a combination thereof. In another embodiment, the agent comprises a bioactive macromolecule such as a DNA plasmid, a single- or double-stranded RNAi molecule, an antisense molecule, an antibody, a carbohydrate, a protein, or a peptide, or a combination thereof. In still another embodiment, the agent is hydrophilic. In still another embodiment, the agent is not lipophilic.

In a further embodiment, the agent comprises an oligonucleotide, which refers to a nucleic acid molecule of length less than about 100, about 200, about 300, or about 400 nucleotides. Non-limiting examples of oligonucleotides include antisense, aptamer(s), siRNA, miRNA, or single-stranded RNAi. As used herein, the term "oligonucleotide" encompasses polynucleotides. The active strand of the nucleic acid can, for example, be a phosphodiester, with an oxygen atom linking consecutive nucleotides. The phosphodiester can, in still a further embodiment, be modified, for example, by replacing the oxygen-link of the nucleotides with, for example, sulfur to provide a phosphorothioate strand or with, for example, a nitrogen to provide a morpholino.

In an embodiment of the invention, the targeting moiety of the nanoparticle comprises a plurality of biocompatible polymers, proteins, peptides, carbohydrates, antibodies, or small molecules. In another embodiment, the targeting moiety does not comprise a lipid derivative. As used herein, the terms "targeting moiety" and "ligand" are used interchangeably.

In still another embodiment of the invention, the targeting moiety is tenascin. Tenascin ("TN") is an extracellular matrix molecule that is useful for nanoparticles as a biocompatible polymer and/or as a targeting moiety. Tenascin is a branched, 225 KD fibronectin-like (FN) extracellular protein prominent in specialized embryonic tissues, wound healing, and tumors. In the adult, normal cells, aside from wound-activated keratinocytes, do not migrate on tenascin. However, integrin receptors capable of mediating migration on TN by carcinoma cells include $\alpha 2\beta 1$, $\alpha v1\beta 3$ and $\alpha v1\beta 6$. In one embodiment, TN nanoparticles deliver nucleic acids specifically via receptor-mediated caveolar endocytosis. TN, or any subdomain(s) thereof, is a suitable cell recognition polypeptide according to an embodiment of the invention.

Tenascin has been implicated in cancer activities and, also, as being specific for smooth muscle cells; furthermore, peptidic domains of tenascin have been identified (e.g., as in U.S. Pat. No. 6,124,260) and are known in the art. In one embodiment, tenascin suitable for the present invention is *H. sapiens* tenascin C, Genbank Accession No. NM_002160. Moreover, tenascin peptides and domains for adhesion with particular cell types, as well as functional and structural aspects of tenascin, have been disclosed and are known in the art (e.g., Aukhill, et al., 1993 *J. Biol. Chem.* 268(4): 2542-2553). Tenascin and/or any of its domains are, in additional embodiments, suitable for the present invention. In one embodiment, the ligand is the fibrinogen fragment of tenascin (also referred to herein as Fbg-L domain of tenascin-C or tenfibgen or TBG (nucleotide sequence of tenfibgen as disclosed in U.S. patent application Ser. No. 13/071,067), is used as the biocompatible polymer and/or the cell recognition polypeptide. Tenascin, its subdomains, or any other biocompatible polymer may be expressed or produced by methods provided herein, as well as by methods known in the art.

In another embodiment of the invention, hyaluronan is included as the targeting moiety for the nanoparticles of the present invention. Hyaluronan is a negatively charged glycosaminoglycan that can reach a molecular mass of several million Daltons and is a ubiquitous component of extracellular matrices. This carbohydrate is commercially available in a variety of forms and has many known uses (e.g., U.S. Pat. No. 5,902,795). In one embodiment of a method according to the invention, the hyaluronan used is a low molecular weight hyaluronan. It is found herein that such low molecular weight hyaluronan is surprisingly effective for topical administration of vaccines.

In still another embodiment, the targeting moiety is asialoorosomucoid (ASOR) (Stockert, et al. 1980 *Lab. Invest.* 43:556-63), which is capable of targeting hepatic cells of the liver, for example. For example, subcutaneous administration of therapeutic oligonucleotides at low dosages via nanoparticles may be effective in the treatment of liver diseases or diseases involving hepatocytes. As used herein, the term "therapeutic oligonucleotides" describes oligonucleotides that can be used to essentially silence genes and/or to inhibit a portion or all of the activity of proteins that are responsible for a particular disease.

In one embodiment of the invention, the nanoparticles described herein can be used to treat or diagnose disease. In another embodiment, the nanoparticles described herein can be used to treat or diagnose diseases of the liver. For example, the nanoparticles described herein can be used to treat hepatic disease, where treatment comprises administering the nanoparticles for the purpose of regulating, repairing, adding, inhibiting, or deleting a genetic sequence in hepatic tissue and cells. In a separate embodiment, the nanoparticles described herein can be used to diagnose hepatic disease.

In another embodiment, the nanoparticles described herein inhibit the expression of the Factor VII (FVII) gene in a cell or mammal using an oligonucleotide, for example, for treating pathological conditions and diseases caused by the expression of the FVII gene, such as coagulation disorders.

In still another embodiment, the nanoparticles described herein can be used to treat or diagnose diseases other than cancer. For example, the nanoparticles described herein can be used to treat tumors other than primary tumors. In one embodiment, the nanoparticles described herein can be used to topically or subcutaneously treat or diagnose diseases of the lymphatics or lymph nodes, including via judicious selection of a targeting moiety to enhance lymphatic or lymph node uptake.

The nanoparticles described herein are contemplated, in separate embodiments, for use in in vitro, in vivo, and ex vivo applications. In separate embodiments, the nanoparticles described herein can be used to treat a subject in need of induction of an immune response, prevention of disease, protection from effects of infection, therapy of existing disease or symptoms, or combinations thereof.

In another embodiment, the nanoparticles described herein are used to treat, vaccinate, or diagnose a subject, wherein the subject is a mammal. In additional embodiments, the subject is a human or a veterinary mammal.

Nanoparticle sizing may be altered, in one embodiment, by increasing or decreasing the weight of coating ligand applied to the particle during synthesis, and/or increasing or decreasing the length of crystallization time allowed during the precipitation and hardening step. A less preferable but still viable method for altering the size of the nanoparticles disclosed herein can be achieved by increasing or decreasing the amount of condenser used in mixing with, for example, nucleic acid cargo, to form the core of the particle. In certain additional embodiments, reducing the size of the nanoparticles described herein may increase the plasma concentration of topically or subcutaneously administered nanoparticles. In certain additional embodiments, increasing the size of the nanoparticles described herein may increase the lymphatic concentration of topically or subcutaneously administered nanoparticles.

In some embodiments, a method of treating or diagnosing disease is provided comprising administering the nanoparticles to a host in a single dose once a day or more frequently. In some embodiments, the nanoparticles are administered less than once a day. In some embodiments, the nanoparticles are administered in a depot that provides efficacious dosage without repeated injections. In some embodiments, including plasmids coding for antigenic sequences or therapeutic sequences, administration to a subject may comprise single or repeat dosing.

As used herein, the term "therapeutic sequences" refers to sequences intended to ultimately modulate cellular protein or transcriptions levels, and the plasmids encoding for therapeutic sequences are termed "therapeutic plasmids". Non-limiting examples of therapeutic plasmids include plasmid DNA, including, for example, shRNA plasmid DNA. Non-limiting examples of diseases that can be treated with s50 particles bearing therapeutic plasmids include cancer and haemophilia. For avoidance of doubt, unless specified otherwise herein, therapeutic sequences do not include antigenic sequences. As used herein, the term "repeat dosing" refers to administering a drug or other substance to a given subject more than once to treat a given disease or disorder, at dosage levels that may or may not vary with each administration.

Methods for identifying oligonucleotide chemistry and sequence to inhibit a desired target are well known to those of skill in the art. For example, conventional antisense design typically optimizes for uniform hybridization energies across sequences at sites of low target mRNA secondary structure, while siRNA design is more focused on optimizing a hybridization profile across a sequence within the context of sequence "rules". Non-limiting examples of design algorithms such as Soligo for antisense and SiRNA for siRNA are publicly available (http:/sfold.wadsworth.org and websites for suppliers such as Dharmacon). Sequence selection then consists of routine optimization in the applicable oligonucleotide formats, followed by nanoparticle formulation, in vitro assessment in target cells plated on conventional 2D or, in a preferred embodiment, relevant protein or 3-D matrices, and/or in vivo assessment in an animal model.

Methods for high-throughput functional screening and identification of potential candidate vaccine antigens from genomic sequence data are well known to those of ordinary skill in the art. In one non-limiting example, transcriptionally active PCR (TAP) and TAP immunoscreening can be used (Regis, et al. 2007 *Mol Biochem Parasitol* 158:32-45). TAP immunoscreening approaches for validation of agents as potential vaccine candidates include for example subcellular localization studies, gene knockout studies, and rodent orthology protection studies.

In some embodiments, extravascular administration of the nanoparticles described herein is achieved by, for example, intramuscular, intradermal, transdermal, transcutaneous, transmucosal, intracerebral, or subcutaneous injection or device-based (e.g., infusion pumps or motor-driven devices) application, or by topical application. It will be understood by those of ordinary skill in the art that these methods of administration refer to how the nanoparticles are applied to the subject, and not where they remain or traverse to. In some embodiments, administration according to the invention is performed by extravascular administration other than topical administration, for treating cancer and for treating other diseases.

As mentioned above, extravascular indicates administration other than intravenous. In one embodiment, administration of the nanoparticles is performed by subcutaneous administration by needle, syringe, catheter, or similar device, with or without the aid of an infusion pump or motor-driven device, and/or with or without the aid of penetration enhancing agents. Penetration enhancing agents for subcutaneous administration are well known to those of ordinary skill in the art. Non-limiting examples of penetration enhancing agents for subcutaneous treatment include hyaluronidase or hyaluronidase glycoproteins.

As the skin is the largest and most accessible organ, it provides an attractive target for drug and vaccine development. However, an effective physical barrier in the epidermis protects against the entry of environmental substances, including nucleic acids. In particular, large hydrophilic molecules such as most biopharmaceuticals normally do not pass through the skin. These challenges emphasize the need for an easily applied system for delivering drugs or vaccines that is able to transit the stratum corneum.

Current strategies to overcome the challenges of transiting the stratum corneum include physical methods that disrupt the barrier properties of the stratum corneum by mechanical means, such as electroporation, liquid jet device, biolistic, or abrasive tape strip, or by microporation approaches that may comprise approaches such as solid or hollow microneedles, thermal energy, or radiofrequency. Other strategies include the use of skin penetration enhancers, such as enzymatic penetration enhancers and/or chemical penetration enhancers, such as solvents and surfactants.

These strategies for crossing the stratum corneum have met with little success because of associated cell damage, poor tissue distribution, and/or cellular uptake, off-target delivery, high treatment pain, and other factors. Therefore, in certain embodiments of the present invention, the nanoparticles can be co-administered with physical methods including mechanical means and/or microporation means, and/or with external skin penetration enhancers, to enable and/or increase the utility of these strategies including less cell damage, improved tissue distribution and/or cellular uptake, increased targeting, lower dosages, and reduced treatment pain. For example, loading a microneedle array patch with nanoparticles may, upon administration, increase the tissue distribution of the cargo, increasing efficacy and potentially reducing dose and/or number of required treatments (and therefore, reducing the number of invasive treatments). Those of ordinary skill in the art will appreciate that the nanoparticle compositions described herein may be readily incorporated or formulated with such physical methods and skin penetration enhancers.

As disclosed herein, the nanoparticles can also cross the stratum corneum and/or mucous membranes after topical application. Thus, in certain embodiments, the nanoparticles described herein may be topically administered to intact, unbroken skin. In further embodiments, topical administration of the nanoparticles does not comprise the use of physical methods and/or external enzymatic penetration enhancers and/or external chemical penetration enhancers, thus potentially reducing or avoiding cell damage, treatment pain, and other adverse reactions at the site of treatment.

In certain embodiments, the nanoparticles are topically administered with facilitating agents, which are well known to one skilled in the art and include, without limitation, lotions, ointments, creams, pastes, sprays, gels, pipettes, and/or patches, where such agents may or may not include enzymatic and/or chemical skin penetration-enhancers. In certain embodiments, facilitating agents may further improve bioavailability and/or uniformity of delivery. As used herein, the term "bioavailability" refers to the degree to which a drug or other substance becomes available to the target tissue after administration. In one embodiment, hydration of the skin before, during, or immediately after application of such a formulation is desirable. For example, hydration may increase the water content of the topmost layer of skin (e.g., stratum corneum or superficial epidermis layer exposed by penetration enhancement techniques) to above about 1%, about 5%, about 10%, about 25%, about 50%, or about 75%. It is to be understood that uses of the nanoparticles disclosed herein are contemplated to include standard methods for cleaning, sterilizing, etc. the subject's area of treatment before, during, or after administration of the nanoparticles, as necessary. In certain embodiments, the surface area to be treated is shaved before administration. In other embodiments, the surface area to be treated is not shaved before administration.

As used herein, "topical" administration refers to administration of the nanoparticles or a composition comprising the nanoparticles to a surface such as the skin or mucous membranes such as the vagina, anus, throat, and ears. "Passive topical" administration refers to topical administration without the use of physical methods, such as mechanical and microporation methods, that disrupt the barrier properties of the stratum corneum and/or mucous membranes. The term "active topical" administration refers to administration of the nanoparticles or a composition comprising the nanoparticles with the use of physical methods, such as mechanical and/or microporation methods, that disrupt the barrier properties of the stratum corneum and/or mucous membranes.

The term "without external enhancers" refers to embodiments and methods, such as topical delivery, that do not comprise the use of external enzymatic penetration enhancers and/or external chemical penetration enhancers for the skin and/or mucous membranes. It is to be understood that the external enhancers excluded by the term "without external enhancers" do not include water used primarily for hydrating the skin and/or mucous membranes during pre-treatment, co-treatment, or post-treatment.

In separate embodiments, the nanoparticles may be administered extravascularly, including topically (passive and active topical, in separate embodiments), to a subject for the purpose of delivering DNA, protein, peptide, or carbohydrate antigen cargos in the process of vaccination. As used herein, the terms "DNA antigen" and "antigen comprising DNA" refers to a DNA plasmid that encodes an antigenic sequence.

In certain embodiments, the extravascularly administered nanoparticles provide co-stimulation of specific humoral and cell-mediated responses. In one embodiment, an immune response, subsequent to extravascular administration of the nanoparticles described herein, is observed in primary sites, including blood, skin and mucosal tissue. In another embodiment, an immune response, after extravascular administration of the nanoparticles, is observed in disseminated tissue, including draining and distal lymph nodes.

The nanoparticles described herein may also be administered in a non-clinical setting, such as in military field operations. In certain embodiments, the nanoparticles may be stored in ready-to-use formulations that do not require refrigeration for periods of about 6 months, about 12 months, about 18 months, about 24 months, about 36 months, or about 60 months. In one embodiment, nanoparticles encapsulating DNA antigen are administered by topical, subcutaneous, or intradermal injection as a priming step, followed by topical application in one or more boosting steps. In an additional embodiment, the nanoparticles comprise a ligand for spleen targeting to enhance specific IgG responses to the encapsulated antigenic protein or DNA cargo.

In one embodiment, the nanoparticles described herein comprise antigenic protein or DNA cargo and modulate IgA, IgD, IgE, IgG, and/or IgM responses. In another embodiment, the nanoparticles comprise a nickel adjuvant. In still another embodiment, the nanoparticles are administered by an extravascular method, such as, for example, a topical method, to treat a disease that requires modulation of IgA, IgD, IgE, IgG, and/or IgM responses to be effective. In another embodiment, the nanoparticles administered extravascularly may be indicated to vaccinate subjects who cannot tolerate treatment-site reactions. Determination of such subjects can be made by a physician or other qualified individual based on, for example, the subject's treatment history and/or medical or physical condition.

An "immune response" is defined as a response of a cell of the immune system, such as a B cell or a T cell, to a stimulus. An immune response can be measured by several parameters, including, but not limited to, cytokine secretion (IL-6, IL-10, IFN-$\alpha$, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of (3)H-thymidine can be assessed.

A "substantial" increase in a parameter of the immune response is a significant increase in this parameter as compared to a control. Specific, non-limiting examples of a substantial increase include at least about a 25% increase, at least about a 50% increase, at least about a 75% increase, at least about a 90% increase, at least about a 100% increase, at least about a 200% increase, at least about a 300% increase, and at least about a 500% increase. One of skill in the art can readily identify a significant increase using known statistical methods. For example, to assess a substantial increase, a Z test can be used to compare the percent of samples that respond to a formulated vaccine contemplated for administration according to a method of the invention as compared to the percent of samples that respond to a control. A non-parametric ANOVA can be used to compare differences in the magnitude of the response induced by the vaccine as compared to the percent of samples that respond using a control. In this example, p less than or equal to 0.05 is significant, and indicates a substantial increase in the parameter of the immune response. One of skill in the art can readily identify other statistical assays of use.

In certain separate embodiments, the nanoparticles contemplated for extravascular administration comprise a plurality of low molecular weight hyaluronan ligands averaging less than about 50,000 Daltons, less than about 40,000 Daltons, less than about 30,000 Daltons, less than about 25,000 Daltons, less than about 20,000 Daltons, less than about 15,000 Daltons, less than about 10,000 Daltons, between about 5,000 and 30,000 Daltons, or between about 10,000 and 30,000 Daltons. In a specific embodiment, the hyaluronan ligand has a molecular weight of 22,480 Daltons. The nanoparticles can be formulated for this range of hyaluronan molecular weight, for example, by adjusting minor components (dopants) in the crystallization bath.

In one embodiment, nanoparticles such as topical hyaluronan-nickel nanoparticles provide a universal strategy for engaging the immune system in the vaccination process. This strategy improves efficacy and flexibility for addressing a range of diseases by judicious design and selection of the DNA plasmid or protein antigen. Thus, the nanoparticles described herein can be used as vaccines for control of diseases such as infectious diseases, including, without limitation, Chlamydia, Cytomegalovirus, Helicobacter Pylori, Herpes Simplex, Papillomavirus, Influenza, Meningococcus B, nvCreutzfeldt-Jakob Disease, Respiratory Syncytial Virus, Severe Acute Respiratory Syndrome, Shigella, Turberculosis, West Nile, and Zoster. In another embodiment, hyaluronan-nickel nanoparticles are administered extravascularly for tumor treatment.

In another embodiment, the targeted, antigen-bearing nanoparticles of the present invention are used in topical or other extravenously-administered treatments other than tumor treatment.

In certain separate embodiments, vaccine nanoparticles contemplated for extravascular, including topical, administration for prophylactic and/or therapeutic use comprise an amount of antigen in a unit dose anywhere in a range from about 0.001 µg to about 10 mg, from about 0.1 µg to about 1 mg, from about 5 µg to about 500 µg, between about 1 µg and about 10 µg, between about 10 µg and about 50 µg, between about 50 µg and about 200 µg, and between about 1 mg and about 5 mg. In one embodiment, the amount of antigen in the unit dose is about 100 µg. In one embodiment, the amount of antigen in the unit dose is about 500 µg.

In certain embodiments, vaccine nanoparticles for topical administration may be administered in an application that covers from about 0.001% to about 100% of the subject's total body surface area, or between about 0.001% and about 90% or about 80% or about 70% or about 60% or about 50% or about 40% or about 30% or about 25% or about 20% or about 15% or about 10% or about 5% of the subject's total body surface area, or between about 5% and about 30% or between about 5% and about 20% of the subject's total body surface area. In one embodiment, the topical vaccine preparation is applied to cover about 5% or about 10% or about 20% or about 30% or about 100% of the subject's total surface area. In a certain embodiment, the topically-applied nanoparticle vaccine preparation does not cover all or substantially all of the subject's total surface area. In certain embodiments, the concentration of the antigen applied in a unit dose is between about 0.001 and about 100 µg/sq cm of treated surface area, between about 0.01 and about 50 µg/sq cm of treated surface area, between about 0.01 and about 25 µg/cm of treated surface area, less than about 10 µg or about 8 µg or about 5 µg or about 3 µg or about 1 µg/sq cm of treated surface area, or about 0.44 µg/sq cm of treated surface area. The ratio of adjuvant to antigen in a unit dose will vary depending on the strength of each, but non-limiting examples include nanoparticles formulated with an adjuvant amounting to less than about 5% of the antigen by weight, less than about 1% of the antigen by weight, or less than about 0.1% by weight.

In some embodiments, the efficacy of the topical vaccine nanoparticles can be enhanced or optimized by modifying the concentration of antigen being applied. In applications where the vaccine nanoparticles are to be sprayed on the surface of the subject, non-limiting examples of the concentration of the antigen to PBS or other acceptable diluents are between about 1 µg/ml to about 10 mg/ml, between about 25 µg/ml to about 200 µg/ml, between about 25 µg/ml to about 100 µg/ml, about 50 μg/ml. For compounding into solid dosage forms, non-limiting examples of concentration of the antigen to the solid dosage form are between about 10 μg/ml to about 100 mg/ml, between about 100 μg/ml to about 10 mg/ml, between about 0.5 mg/ml to about 10 mg/ml, between about 0.5 mg/ml and 5 mg/ml, about 1 mg/ml.

With regard to formulations comprising other therapeutic plasmids, the nanoparticles described herein can be administered subcutaneously in a unit dose selected from a range of between about 0.01 mg/kg and about 50 mg/kg, between about 0.1 mg/kg and about 30 mg/kg, between about 1 mg/kg and 20 mg/kg, between about 5 mg/kg and about 20 mg/kg, between about 5 mg/kg and about 30 mg/kg, about 1 mg/kg, about 10 mg/kg, about 20 mg/kg, less than or equal to about 30 mg/kg, less than or equal to about 20 mg/kg, more than or equal to about 1 mg/kg, about 5 mg/kg, and about 10 mg/kg. In one embodiment, the dose is about 20 mg/kg.

In embodiments involving other therapeutic applications, including formulations comprising oligonucleotides, the nanoparticles described herein can be administered in a unit dose of about 0.00001 mg drug/kg body weight, about 0.0001 mg/kg, about 0.001 mg/kg, about 0.01 mg/mg, about 0.1 mg/kg, about 1.0 mg/kg, about 2.0 mg/kg, about 3.0 mg/kg, about 4.0 mg/kg, or about 5.0 mg/kg, less than or equal to about 1.0 mg/kg, less than or equal to about 2.0 mg/kg, or less than or equal to about 5.0 mg/kg.

Non-limiting examples of methods for improving dosage include optimizing sequence and medicinal chemistry. For example, the incorporation of a 2'-β-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, in one embodiment, functionalized, linked nucleosides can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group.

The improved bioavailability and targeting of the nanoparticles contemplated for extravascular administration, combined with flexibility in incorporating various cargoes and ligands, provides for the potential treatment of a wide range of diseases. Non-limiting examples of diseases the nanoparticle formulations can be used to treat include hepatitis, cancer, atherosclerosis, tuberculosis, and asthma.

In some applications, the nanoparticles described herein are administered to a subject who has cells that are expressing or over-expressing a particular receptor that is indicative of a disease state, and which can be targeted by judicious selection of nanoparticle ligand. For example, a subject with cells that express or over-express tenascin receptors may have cancer. Methods for diagnosing or detecting tenascin or tenfibgen receptors are provided herein.

A variety of cancers may be diagnosed or detected by measuring tenascin or tenfibgen expression levels, where the over-expression level of tenascin or tenfibgen indicates a cancer diagnosis, and/or where the expression level of tenascin or tenfibgen indicates a target for tumor-targeted nanoparticles according to certain embodiments of the invention. By "over-expression" is meant an increase in, for example, expression of a particular molecule, e.g., tenascin or tenfibgen, relative to a control, e.g., relative to the level of expression that is normally produced by non-cancerous cells. The exact amount of over-expression or increase is not necessarily critical, as long as the over-expression or increase is statistically significant. Diagnostic methods for cancer and the clinical delineation of cancer diagnoses are known to those of ordinary skill in the art.

Assays according to some embodiments of the invention may be carried out in vivo, in vitro, or ex vivo using samples obtained from standard sources and by standard procedures. A "sample" can be any organ, tissue, cell, or cell extract isolated from a subject, such as a sample isolated from a mammal having a cancer. For example, a sample can include, without limitation, cells or tissue (e.g., from a biopsy or autopsy) from plasma, organ or tumor, or any other specimen, or any extract thereof, obtained from a patient (human or animal), test subject, or experimental animal. In some embodiments, it may be desirable to separate cancerous cells from non-cancerous cells in a sample.

A "control" includes a sample obtained for use in determining base-line expression or activity. Accordingly, a control sample may be obtained by a number of means including from non-cancerous cells or tissue, e.g., from cells surrounding a tumor or cancerous cells of a subject; from subjects not having a cancer; from subjects not suspected of being at risk for a cancer; or from cells or cell lines derived from such subjects. A control also includes a previously established standard. Accordingly, any test or assay conducted according to an embodiment of the invention may be compared with the established standard, and it may not be necessary to obtain a control sample for comparison each time.

Tenfibgen or tenfibgen expression or activity can be assayed using a variety of techniques, including immunohistochemistry (IHC), in situ hybridization (ISH), Northern blotting, polymerase chain reaction (e.g., real time quantitative PCR or RT-PCR), antibody-based assays, such as immunoprecipitation, immunofluorescence, Western blotting, nucleic acid sequencing, etc.

In some embodiments, cells in a subject may be exposed in vivo to an antibody (e.g., a tenfibgen or tenascin antibody, or a tenfibgen-coated nanoparticle at about 10 µg/µl of oligonucleotide concentration), which is optionally detectably labeled, e.g., radioactive isotope; and binding of the antibody to the cells may be evaluated by, e.g., external scanning for radioactivity or analysis of a biopsy.

The assays may be conducted using detectably labelled molecules, i.e., any means for marking and identifying the presence of a molecule, e.g., an oligonucleotide probe or primer, a gene or fragment thereof, a peptide, or a cDNA molecule. Methods for detectably labelling a molecule are known in the art and include, without limitation, radioactive labelling (e.g., with an isotope such as $^{32}P$ or $^{35}S$) and non-radioactive labelling such as enzymatic labelling (for example, using horseradish peroxidase or alkaline phosphatase), chemiluminescent labeling, fluorescent labeling (for example, using fluorescein), bioluminescent labeling, or antibody detection of a ligand attached to the probe. Also included in this definition is a molecule that is detectably labelled by indirect means, for example, a molecule that is bound with a first moiety (such as biotin) that is, in turn, bound to a second moiety that may be observed or assayed (such as fluorescein-labeled streptavidin). Labels also include digoxigenin, luciferases, and aequorin.

The term "detecting", as used herein, is intended to include determining the presence or absence of a substance and/or quantifying the amount of the substance. The term, thus, refers to the use of the materials, compositions, and methods according to certain embodiments of the invention for qualitative and quantitative determinations. In general, the particular technique used for detection is not critical for practice of the invention. Detecting may include quantifying a change (increase or decrease) of any value between about 10% and about 90%, or of any value between about 30% and about 60%, or over about 100%, when compared to a control. Detecting may include quantifying a change of any value between about 2-fold to about 10-fold, inclusive, or more, e.g., about 100-fold.

As used herein, an "effective amount" or "therapeutically effective amount" is defined as an amount effective, at dosages and for periods of time necessary, to produce the intended pharmacological, therapeutic or preventive result. For example, if a given clinical treatment is considered effective when there is at least about a 25% reduction in a measurable parameter associated with a disease or disorder, a therapeutically effective amount of a drug for the treatment of that disease or disorder is the amount necessary to effect at least about a 25% reduction in that parameter. The effective amount of the formulated drug, vaccine, or imaging agent of the invention may vary according to factors such as the disease state, age, sex, and weight of the subject. The precise amount and number of doses and timing can be readily determined by those skilled in the art. With regard to topically applied vaccines, factors influencing dosing include, without limitation, the chemical structure and biological activity of the antigen and adjuvant, the concentration of the application, the body site to be treated, the surface area, age, weight, and treatment history of the subject, and the precise condition requiring treatment and its severity.

Dosage regimens may be adjusted to provide the optimum response. For example, doses may be one-time or multi-dose, or several divided doses may be administered daily, or the dose may be proportionally reduced as indicated by the exigencies of the medical situation. An effective amount of antigen sufficient to induce an immune response may be delivered, for example, at a single cutaneous and/or mucous membrane location, or at multiple cutaneous and/or mucous locations, or, in a separate embodiment, over an area of skin covering multiple draining lymph node fields (e.g., cervical, axillary, inguinal, epitrochelear, popliteal, mandibular, those of the abdomen and thorax). Such locations close to numerous different lymphatic nodes at locations all over the body may provide a more widespread stimulus to the immune system than when a small amount of antigen is injected at a single location intradermally, subcutaneously, or intramuscularly.

Example 7 describes a study using three courses of 500 µg plasmid DNA antigen encapsulated in sub-50 nanometer nanoparticles comprising a low-molecular weight hyaluronan shell spiked with nickel for adjuvant effect, administered in a weanling pig model via passive topical application. IgG titers generated with this formulation were within one log of standard intradermal protein treatment (3× at 500 μg), and were two-fold the titer level generated by intradermal naked DNA treatment (3× at 500 μg). Specific IgA response was persistent and 2.5× vs. naked intradermal DNA by grand average while specific lymphocyte response was 37× for draining nodacytes and 12.1× for distal nodacytes (p<0.05) over standard intradermal protein inoculation. No treatment site reactions were found after topical administration at the end of the 7-week study.

The artisan will recognize the methods and results for weanling pigs are relevant to other mammal models, including humans. For example, with regards to the relevance to humans, the physiology of the skin is known to be very similar between humans and pigs, and the development of the immune system is also similar between humans and pigs.

In one embodiment, a method according to the invention includes evaluating the subject for lymph node concentration and/or plasma concentration of the administered drug or diagnostic agent. Such an evaluation can, for example, be performed before, during, and/or after the administration of the agent. For example, the evaluation can be performed at least about 1 day, about 2 days, about 4, about 7, about 14, about 21, or about 30 or more days before and/or after the administration.

Treatment site reactions can occur when a therapeutic is deposited, for example, in the subcutaneous tissue or topically on the tissue of a subject. In one embodiment, the extravascular administration of the nanoparticles described herein avoids or diminishes such reactions, due to low dosage, effective tissue clearance, absence of prolonged treatment-site retention due in part to the crystal nature and/or essentially neutral charge of the nanoparticles, and/or other factors.

Furthermore, the volume of subcutaneous injection is limited (e.g., in humans, subcutaneous injection is limited to about 1 mL) because of the pain and tissue distortion, irritation, and redness (erythema) that accompany large volumes. This limitation prevents subcutaneous delivery of drugs which typically require high dosages. Thus, in an embodiment of the present invention, the nanoparticles described herein enable subcutaneous delivery of such high-dose drugs, due to more effective biodistribution, less aggregation at or near the injection site, and, in comparison to other nucleic-acid delivery technologies, more efficient packaging of the drug in the nanoparticle (e.g., where the encapsulated drug accounts for more than about 60%, more than about 70%, more than about 80%, more than about 85%, or more than about 90% of the weight of the nanoparticle). In separate embodiments, the formulations described herein are suitable for subcutaneous administration volumes of about 2 mL, about 5 mL, about 10 mL, about 20 mL, and between about 2 and about 20 mL.

Also provided herein, in additional embodiments, are diagnostic agents and methods of use to improve the utility and accuracy of diagnostic imaging techniques in research and medical applications. Generally, diagnostic agents are agents that can be detected or observed following administration into a cell, tissue, organ, or mammal. Diagnostic agents include contrast agents, which are used to improve the visualization of cells, tissues, organs, and physiologic processes by increasing the relative difference of imaging signal intensities in adjacent regions of the body. Diagnostic imaging techniques of the nanoparticles described herein can be used, for example, in the identification, planning, staging, treatment, and monitoring of, for example, lesions or other areas of abnormal tissue. For example, diagnostic imaging techniques may be used in the treatment of patients with tumor lesions, including where the treatment consists of chemotherapy, surgery, and/or radiation therapy.

Diagnostic techniques can also be used in molecular imaging, which is broadly defined as characterization and measurement of the biologic processes of disease by assessing functional (e.g., vascularization, blood flow and lymphatic flow), metabolic (e.g., glycolysis and tumor viability), or molecular phenomena (e.g., proliferation, epidermal growth factor receptor expression and apoptosis, at the cellular and molecular level).

In some embodiments, the nanoparticle diagnostic agent comprises a core comprised of dysprosium or dysprosium derivatives associated with a functionalized chelating ligand complex, wherein the functionalized chelating ligand complex is comprised of a covalently-bound functionalized chelating ligand and a polymer comprised of dextran or derivatives of dextran; a surfactant substantially surrounding the core to form a surfactant coated complex, wherein the surfactant has an HLB value of less than about 6.0 units; and a shell which non-covalently adheres to and substantially surrounds the surfactant-coated complex, wherein the shell comprises a precipitate comprising a targeting moiety and a cationic precipitating agent, wherein the cationic precipitating agent is comprised of lithium.

In some embodiments, a water-soluble polysaccharide other than dextran can be used. Non-exhaustive examples of such a polysaccharide would include mannose and sucrose.

In another embodiment, the chelating ligand is chosen from the group of diethylenetriamine tetraacetate (DTTA), diethylenetriamine pentaacetate (DTPA), 1,4,7,10-tetraazacyclododecane-1,4,7,10-tetraacetic acid (DOTA), 1,4,7,10-tetraazacyclododecane-1,4,7,10-tetrakis(2-propionic acid) (DOTMA), and 1,4,8,11-tetraazacyclododecane-1,4,8,11-tetraacetic acid (TETA).

In further embodiments, methods of using the nanoparticle diagnostic agents include analyzing a cell, a tissue, or a subject, the methods comprising administering to a cell, a tissue, or a subject a nanoparticle diagnostic agent and subjecting the cell, tissue, or subject to fluorescent imaging, neutron activation analysis (NAA), and/or related applications, and analyzing the resulting information to detect, diagnose, monitor, or report on a parameter of a cell, a tissue, or a subject. The use of the nanoparticle diagnostic agents disclosed herein as fluorescent (optical) agents is surprising, as dysprosium is not known to possess useful fluorescent properties. Relative to other water-quenched lanthanides, dysprosium luminescence is considered the least stable, with a time constant of only 9-11 μsec in aqueous media. Without wishing to be bound by theory, it is believed the nanoparticle diagnostic agents described herein are not subject to the some or all of the complications of photobleaching, photodegradation, and diffusion that are typically associated with the use of optical imaging dyes and protocols.

In one embodiment, the nanoparticle diagnostic agents of the present invention are used as a tissue marker to mark a position in a body, such as a specific position in a tissue or organ, in order to allow re-visiting of the position to check for progress or developments of an ailment or a treatment, or to allow re-treatment at the same site. For example, tissue marking can be used during a biopsy or other tissue removal procedure to accurately mark the site of the tissue removal or biopsy, thus allowing later return to the same site if desired, in order, for example, to monitor the status of the tissue in question or to carry out a further biopsy. A tissue marker may be viewed broadly as a type of imaging agent that does not move or stays substantially in the same position once it has been administered or implanted. It is often desirable that the tissue marker is biodegradable over a period of time and is resorbed safely by the body.

In another embodiment, the nanoparticle diagnostic agents disclosed herein are used in and/or administered to an aqueous environment, such as a mammal including, for example, a human. In additional embodiments, agents are used in imaging and/or diagnosis, wherein a sample is subjected to imaging outside of the human or animal body. This includes, for example, uses wherein a sample has been removed from the human or animal body or generated outside of the human or animal body.

In certain embodiments, the nanoparticle diagnostic agents are used in optical imaging techniques such as, for example, near infrared (NIR) imaging. This technique involves excitation of a fluorophore that emits light at a wavelength in the red or far red end of the light spectrum (longer than 600 nm). This is a desirable range, as red light passes through living entities better by avoiding absorption by common substances such as hemoglobin. Equipment suitable for optical imaging is well-known in the art and generally consists of a light source, filters, detector, and appropriate electronics for signal processing. Commercial systems such as the Kodak Carestream FXpro, MAESTRO and Xenogen systems are readily available. Key operating parameters for the inventive nanocapsule-based Dy composition include optimal excitation in living creatures at 510 nm and emission at 700. Multispectral analysis to extract the Dy-specific signal is typically supplied with the imaging system and is very beneficial to use. Following dosing which may range from about 10 nmol Dy/kg to about 1 mmol Dy/kg of body weight and a desired amount of time for capsule binding to occur which may last from about 1 minute to about 5 days, image capture is executed for an exposure period that may last from about 1 second to about 15 minutes.

The s50 nanoparticle chemistry together with Dy-chelated cargo provides the important advantage and benefit of facile preparation methods, incorporating proteins, peptides, antibodies, carbohydrates, or small molecules as ligands in the shell. Ligands may be readily exchanged for diagnostic purposes in s50 ligand-targeted particles, e.g., tenfibgen or ASOR may be substituted for an anti-PSA antibody as a ligand to enable a diagnostic imaging agent or theranostic capable of identifying patient populations for treatment guidance.

In another embodiment, methods are described for bulk quantitation of target cells (e.g., tumor cells) in tissue by analytical methods (e.g., ICP-AES, Neutron Activation Analysis (NAA)). It has been discovered that the s50 capsule together with Dy-chelated cargo such as DyDex also provides high sensitivity in NAA (Dy detectable to 0.1 ppb). Without wishing to be bound by theory, this physical characteristic derives, in part, from the large size of the Dy nucleus, enabling it to function as a favorable target for neutron bombardment and activation. This feature enables measurement of Dy cargo as an isotopic tracer by quantitative method. Such bulk measurement would improve sensitivity of detection over spot sampling methods such as tissue sectioning and microscopic observation.

Results presented herein demonstrate the quantitative nature of Dy cargo as a tracer and suggest methods for bulk quantitation. Tissue samples may be ashed, dissolved in dilute nitric acid, and detected for Dy sensitively using established ICP-AES methods. For neutron activation analysis, tissues are simply weighed and shipped to a fusion reactor facility for neutron bombardment and measurement of metastable Dy-163 gamma spectra. Additionally, in line with the multi-modal nature of Dy detection, these bulk measurements can be readily correlated with current microscopy-based methods of detection, due to the long-term retained fluorescence of Dy within the hydrophobic environment within the s50 capsule within formalin-fixed tissue. For example, the use of tumor-targeted capsules bearing fluorescent Dy cargo has been administered in tumor margin analysis post-resection. Dy has excitation peaks at 320 nm and 510 nm with emission peaks at 547 nm and 720 nm. Therefore, both conventional fluorescence microscopy based on mercury-arc illumination with a broad UV excitation emission filtering in the range of 547, e.g., Cy3, Texas Red or confocal microscopy based on yellow laser excitation (514 nm) and image capture at either 547 nm or about 720 nm is feasible.

The utility of the Dy-bearing s50 particle as a diagnostic agent for detecting and quantitating cargo at specific organ locations by extravascular routes is demonstrated in Example 5, where Dy was transferred into the body of mice by both topical and subcutaneous routes, as well as intravenous. Example 5 further demonstrates the utility of s50 Dy agents (here, delivered i.v.) for optical (NIR) imaging of internal organs such as liver and gall bladder in a mouse model. Taken together, those of ordinary skill in the art will appreciate from these results that the s50 Dy particle can be used for optical imaging methods such as, for example, NIR, as well as for detection methods such as NAA, by a variety of routes of administration, and that the s50 Dy particle provides utility for as a diagnostic agent in extravascular, as well as intravenous, applications.

In another embodiment, the nanoparticles described herein are used to identify and measure the disease-fighting capacity of the organ or tissue or cell of interest by delivering a diagnostic payload to a target that corresponds with the disease-fighting capacity of the organ or tissue or cell of interest.

In additional separate embodiments, the nanoparticles contemplated for extravascular administration are used for uptake into cells by lipid rafts, for avoidance of endosomal entrapment, and/or for delivery to the nucleus and/or the cytoplasm of the cell.

In one embodiment, the nanoparticles described herein are administered extravascularly to treat chronic diseases such as cardiovascular or metabolic (e.g., diabetes) diseases, where intravenous delivery is not desirable due, for example, to cost, convenience, or other factors.

The following is a brief description of methods that can be used to make the nanoparticles as disclosed herein. The following description is meant to be representative only and is not meant to be limiting. Briefly, a negatively-charged cargo moiety such as nucleic acid that is to be targeted and delivered to a cell can be complexed with a polycationic polymer to condense or reduce its size to about 50 nm or less. A number of different polycationic polymers (also known as "condensing" agents or proteins) can be used and are well-known in the art. See, for example, Rolland (1998, *Crit. Rev. Therapeutic Drug Carr. Syst.*, 15:143-198). For example, enough polycationic condensing protein can be complexed with the negatively-charged cargo moiety to neutralize at least about 75% (e.g., about 80%, about 85%, about 90%, about 95%, about 99%, or about 100%) of the negatively-charged cargo moiety, which, for nucleic acids, can be measured by ethidium dye exclusion (1998 *J. Controlled Release* 53:289-99). Non-limiting examples of condensers include spermine, polyornithine, and protamine. Simply by way of non-limiting example, 125 µg of 10 kD polyornithine can be used to condense 500 µg of a 20-mer oligonucleotide or 87.5 µg of spermine may be used to condense 250 µg of a 14 kD siRNA oligo. For cargo moieties lacking a negative charge or bearing a positive charge, a condensing polycationic polymer may not be necessary.

An aqueous solution of the complexed or uncomplexed cargo moiety can be encapsulated by first dispersing the cargo moiety into a biocompatible, water-miscible solvent using a biocompatible, water-insoluble surfactant system suitable for preparation of an inverted or reverse micelle. Suitable surfactant systems are well-known in the formulation arts as amphiphilic materials that are essentially hydrophobic and characterized by a hydrophile-lipophile balance (HLB) of about 6.0 or less, a critical micelle concentration (CMC) of less than about 200 µM, or a critical packing diameter greater than about 1.

Hydrophobic surfactants and hydrophobic, water-miscible solvents suitable for preparing reverse micelles are described in Pashley & Karaman (2004, In *Applied Colloid and Surface Chemistry*, John Wiley, pgs 60-85), Rosen (2004, In *Surfactants and Interfacial Phenomena*, John Wiley), *The Handbook of Industrial Surfactants* (1993, Ash, ed., Gower Pub), and *Perry's Chemical Engineer's Handbook* (1997, Perry & Green, 7th Ed., McGraw-Hill Professional). In one embodiment, a hydrophobic surfactant can be 2,4,7,9-tetramethyl-5-decyn-4,7-diol (TM-diol) used in a concentration of up to 0.5% by weight of surfactant micelle volume, and a water-miscible solvent can be dimethylsulfoxide (DMSO). In other embodiments, the water-miscible solvent can be acetone, acetonitrile, ethanol, dimethyl acetamide (DMA), tetrahydrofuran (THF), dioxane, and dimethylformamide (DMF).

The concentration of surfactant selected should, in one embodiment, be sufficient to prepare an optically clear nanoemulsion, but not so much as to induce aggregation, since aggregation can lead to overly large nanoparticles.

In some embodiments, the surfactant includes at least one of cetyl alcohol, 2, 4, 7, 9-tetramethyl-5-decyn-4,7-diol, molecules containing an acetylenic diol portion, and blends of 2, 4, 7, 9-tetramethyl-5-decyn-4,7-diol. In some embodiments, the HLB of the surfactant is less than about 5.0. In some embodiments, the hydrophobic surfactant at least partially surrounds or encloses the diagnostic or therapeutic-containing core. In some embodiments, the surfactant complex is at least partially surrounded by the targeting moiety and cationic precipitating agent.

The micelles carrying the cargo moieties can be coated by adsorption with cell-targeting moieties (e.g., proteins, peptides, carbohydrates, or antibodies) by mixing one or more targeting moieties with an aqueous suspension of the micelles. In some non-limiting embodiments, targeting moieties can be mixed with nanocapsules in a ratio (by weight) of about 1 part ligand to about 100 parts drug, to about 1 parts ligand to about 10 parts drug, depending upon the rate at which the nanocapsule is desired to dissolve or disassemble. In one embodiment, the coating weight ratio is about 1:16 of nanocapsules to targeting moieties. In another embodiment, the ratio is about 1:20.

Targeting moieties may also, in some embodiments, be modified by processes designed to enhance final nanoparticle function, e.g., tenascin polypeptides may be precipitated from cell culture supernatants using metal-containing ammonium sulfate such that metals known to promote oxidative stress are adsorbed onto coating ligands preceding nanoparticles preparation. Coating ligands may be readily modified with pharmaceutically acceptable heavy metals by re-precipitating protein in saturated ammonium sulfate solutions prepared with known levels of heavy metals. Incubation of an about 0.1-about 1 mg/ml solution of protein about 1:2 with a saturated ammonium sulfate solution is most expeditiously executed for about 4-36 hours before recovering metal-modified coating ligand by centrifugation. Metal concentrations in the ultrapure ammonium sulfate may range from about 1 part per thousand-about 1 part per trillion.

To stabilize the targeting moiety-adsorbed nanocapsule, the aqueous suspension of nanocapsules coated with one or more targeting moieties can be mixed into an aqueous solution of metal ions (i.e., a "stabilization solution") capable of precipitating, crystallizing, or iontophoretic exchange with the coated nanocapsules. Representative, non-limiting examples of solutes that can be used to precipitate the coated nanocapsules include ionic species derived from elements listed in the periodic table. Ions may be included in the aqueous stabilization composition in a range from about 0.1 part per trillion to about 1 Molar (M). An adequate amount of ion should be included such that the coated nanocapsules are sufficiently contacted with ions, but not so much that aggregation occurs, which can lead to overly large capsules. In one embodiment, a stabilization solution can include about 10 millimolar (mM) Ca2+ and about 200 mM Li+. If ultrapure reagents are used in the stabilization solution, addition of very small amounts (e.g., less than 1 mM) of ions such as Ba, Fe, Mg, Sr, Pb and Zn, normally found in sufficient quantities in preparations of lithium and calcium salts that are not ultrapure, may be added to optimize stabilization of the coated nanocapsules. Addition of cations such as, without limitation, Ni, Bi, Pb, Ur, Al, Ba, and Dy, in the receiving bath can also be useful for manipulating nanoparticle properties. Suitable counterions include chloride, acetate, sulfate, and similar anions. In a certain embodiment for vaccine nanoparticles with 250 μg of plasmid DNA, the cations in the receiving bath are comprised of 135 mM Li+, 9 mM Ca2+, 1.25 nM Sr2+, 10.0 nM Mg2+ and 380 μM Ni2+ (all ultrapure), wherein the counterion for each is chloride.

In some embodiments, the nanoparticles are prepared in a receiving solution for subsequent precipitation and crystallization, wherein the solution comprises $Li^+$ which may range from about 10-about 250 mM, $Ca^{2+}$ which may range from about 1-about 20 mM, $Sr^{2+}$ which may range from about 0-about 1 μM, and $Mg^{2+}$ which may range from about 0-about 1 uM. Suitable counterions for these cations include chloride, acetate, sulfate, and similar anions.

In some embodiments, the nanoparticles described herein do not comprise polyethylene glycol (PEG) or derivatives thereof. In some embodiments, the nanoparticles do not comprise polyethylenimine (PEI) or derivatives thereof.

Any configuration of the nanoparticles that gives rise to an overall compact and/or globular shape having an appropriate morphology is acceptable, including where there is substructure to the nanoparticle, as long as the overall compact shape occurs. When the overall morphology of the nanoparticle comprises a compact shape, the final surface charge approaches about neutral or slightly negative charge. In one embodiment, a final surface charge of neutral or slightly negative is a preferred surface charge for the nanoparticles contemplated herein for extravascular administration. In another embodiment, particles with a charge of between about +2 and about −15 milli electron volts (mev) are desirable. Additionally, any other components that are capable of increasing the stability of the nanoparticles can be included as part of the stabilization solution, such that the final dry average diameter of the nanoparticles is between a range of about 5-about 50 nm by AFM.

For a more consistent size of nanoparticles, the nanoparticles can, in one embodiment, be atomized through a nozzle. Atomization should be sufficient to apply a shear force capable of breaking up flocculated aggregates without so much force as to induce hard aggregates. Those skilled in the art will understand that a particular nozzle diameter will lead to range of feed pressures suitable for atomizing the nanoparticles to a suitable and consistent size. In one embodiment, a nozzle diameter of less than about 250 microns with feed pressures of less than about 10 psi produces suitable nanoparticles. In another embodiment, the nanoparticles can be atomized into a stabilization solution.

The incubation time and temperature may be varied from about 8 hrs to about 7 days to vary the amount of time required for particle dissolution or disassembly in end use. After precipitating, atomizing, and/or incubating the nanocapsules in a stabilization solution, the nanocapsules can be filtered, centrifuged, and/or dried to obtain separate and discrete sub-50 nm nanocapsules. In one embodiment, nanocapsules are incubated for about 2 days at about 4° C., with nominal rotation in 50-ml round-bottomed tubes with salt solution. The resultant nanocapsules can be frozen or dried and reconstituted for later use. In some embodiments, the particles are subjected to one freeze-thaw before sizing analysis. Encapsulation yields can be determined by methods known in the art, including methods of Burton and ICP.

Methods for synthesizing the nanoparticle diagnostic agents disclosed herein include mixing dysprosium or derivatives of dysprosium with amide-terminated dextran or dextran derivatives covalently linked to a functionalized chelating ligand to create a core mixture, subjecting the mixture to purification by a column-based method to create a purified core mixture, disposing into the purified mixture a hydrophobic surfactant to create a surfactant complex mixture, wherein the hydrophobic surfactant has an HLB value of less than about 6.0 units, and mixing the surfactant complex mixture with a precipitating solution comprising a targeting moiety and a cationic precipitating agent comprised of lithium to create a precipitated nanoparticle mixture, resulting in a nanoparticle diagnostic agent comprising the dysprosium-containing core substantially surrounded by the hydrophobic surfactant, which is substantially surrounded by the targeting moiety and cationic precipitating agent.

The disclosed diagnostic agents provide specific targeting, high resolution, and high sensitivity. In addition, the disclosed diagnostic agents are compatible with a range of imaging modalities. Further, the disclosed diagnostic agents provide a modular targeting component that can be readily synthesized for a given biomarker target. The disclosed diagnostic agents also can be used in both an imaging application and in an analytic application, such as histological diagnoses of collected cells for biochemical tests of blood, to validate that the image observed at a given site after administration of the agent consistently and accurately represents accumulation of the agent at that site.

As described above, the nanoparticles of the present invention may be administered topically with facilitating agents that include, without limitation, patches, pipettes, lotions, ointments, creams, sprays, and/or gels. Those of ordinary skill in the art will appreciate that the inventive nanoparticle compositions may be readily incorporated or formulated with such agents. For example, a variety of transdermal patch structures are known in the art. In an additional embodiment of the present invention, a transdermal patch includes an adhesive. Some examples of adhesive patches are well known (for example, U.S. Pat. Nos. 6,010, 715; 5,591,767; 5,008,110; 5,683,712; 5,948,433; and 5,965,154; all of which are incorporated herein by reference). Adhesive patches are generally characterized as having an adhesive layer, which will be applied to a person's skin, a depot or reservoir for holding a pharmaceutical agent, and an exterior surface that prevents leakage of the pharmaceutical from the depot. The exterior surface of a patch is typically non-adhesive.

In another embodiment, the nanoparticles are prepared as a pack or kit, including as an outpatient pack or a kit for self-administration.

Methods of synthesizing nanoparticle vehicles are described in, for example, the following U.S. patents and patent applications and are incorporated herein by reference in their entireties, with modifications as described herein: Unger, U.S. Pat. No. 6,632,671, issued Oct. 14, 2003; as well as U.S. Patent Publication Nos. 20090238883, 20080113932, 20070098713, 20060018826, 20040137071, 20040038303, and 20040023855, U.S. patent application Ser. Nos. 12/525,652, and 12/644,610; and PCT/US2008/052863. Examples of such nanoparticle manufacture are also disclosed herein in the Examples section, below.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The following examples are provided for illustrative purposes only and are not intended to limit the scope of the invention.

Example 1

Preparation of Dysprosium-Chelated Dextran (DyDex)

This method is based on a modification of Armitage, F. E. et al., Bioconjugate Chem 1990 1(6):365-374. Using a 10× molar excess of p-SCN-Bn-Dota (Macrocyclics B-205, MW 688, 0.1M in DMSO) to dextran amino groups, react p-SCN-Bn-DOTA with amino-terminated dextran (Invitrogen D1861, 40 KD) in 0.1 M Sodium bicarbonate pH 9.0. Incubate overnight at 25° C. Optionally, in place of p-SCN-Bn-Dota, p-NH$_2$-Bn-DTPA, p-NH$_2$-Bn-DOTA, p-NH$_2$-SCN-DTPA, p-NH$_2$-Bn-NOTA, p-SCN-Bn-oxo-DO3A, p-NH$_2$-Bn-oxo-DO3A, p-NO$_2$-Bn-DTPA, p-NO$_2$-Bn-DOTA, p-NH$_2$-Bn-DOTA (t-Bu-ester), p-NH$_2$-Bn-DTPA(t-Bu-ester) p-SCN-Bn-NOTA, p-SCN-PCTA p-NH$_2$-PCTA, or other similar compositions may be suitable. Calculation of the activated chelate as 90× molar excess on dextran is also acceptable. Dialyze, using a 3500 MWCO cartridge, against 0.1 M Sodium bicarbonate pH 9.0 for 4 buffer exchanges, then against ddH$_2$O for 4 additional exchanges. Following lyophilization, incubate dextran intermediate in deionized water with a 10× molar excess of 0.1M DyCL3 (Sigma 203173) overnight at 25° C. Dialyze, using a 3500 MWCO cartridge, against deionized water for 4 to 6 exchanges. Lyophilize and weigh product, measuring Dy incorporation by ICP-AES. Yields in this process are approximately 70% by dextran with a 4-4.5% incorporation of Dy by weight.

Example 2

Preparation of Liver-Targeted Nanoparticles for Subcutaneous Administration

This example describes how colloidal formulations of diverse cargos and biocompatible polymers may be generated, for subsequent subcutaneous administration. Nanoparticles were prepared by the "dispersion atomization" method described in U.S. Pat. No. 6,632,671, which is incorporated herein by reference in its entirety, with some modifications. Oligonucleotide preparations were synthesized by Dharmacon (Boulder, Colo.; siFVII and siRFP) and Trilink Biotechnologies (San Diego, Calif.; single strand FVII and siAboB).

Briefly, to prepare each formula below, the following procedures were used:

Formula A,

250 μg of 21 mer, unmodified, double-stranded RNA oligonucleotide (siFVII, Akinc, et. al, 2009 *Mol Ther* 17(5) 872-879), was first complexed with 87.5 μg of 300 MW spermine (Sigma), then was dispersed into 100 μl of sterile water using a water-insoluble surfactant system (2, 4, 7, 9-tetramethyl-5-decyn-4, 7-diol (TM-diol; SE-30 (Air Products), 6.25 μg in 50% DMSO. Following emulsification with 150 μl of a water-miscible solvent (DMSO), the complexes were then inverted and diluted by the addition of 750 μl of PBS.

The resultant hydrophobic micelles were coated (non-covalently) by the addition of 12.5 μg of asialoorosomucoid (ASOR; prepared by the method of Stockert, et al. 1980 *Lab. Invest.* 43:556-63), then atomized into a modified LiCl salt receiving solution (135 mM $Li^+$, 9 mM $Ca^{2+}$, 31.25 nM $Sr^{2+}$, 12.5 nM $Mg^{2+}$ (all ultrapure, Sigma)). Following cold-room incubation (4° C.) with nominal rotation in 50 ml round-bottomed tubes for 48 hours, which stabilizes the coated micelles in the salt solution, the sub-50 nm nanocapsules were recovered by centrifugation at 20,000×g for 2 hrs and resuspended in PBS+10% lactitol (at a concentration of 0.5 μg/μl) for filter sterilization through a 0.2 μm filter. In all formulations described, a small amount (1% of coating weight) of Syrian Hamster Fab fragment was "spiked" into the ligand coat to enable immunodetection of nanocapsules uptake by anti-syrian hamster IgG antibodies. Average capsule size with standard error was about 22.5± about 1 nm, as measured by tapping mode atomic force microscopy using average of minor and major elliptical diameters of a 0.5 ng/ml sample dried down on a mica sheet. Average zeta potential was between about +2 and −15 mev (−5.5±5.4 mev) when measured on Zetasizer 4 dynamic light scattering device at a potential of 20 volts with a 2-second pause between measurements in 1 mM KCl at 2 μg/ml. Encapsulation yield was 100% by the modified method of Burton, Kren, et al. 2009 *JCI* 119(7):2086-99.

Formula B:

sub-50 nm nanocapsules coated with asialoorosomucoid (ASOR; prepared by the method of Stockert, et al. 1980 Lab. Invest., 43:556-63, incorporated herein by reference in its entirety) bearing single-stranded DNA/RNA chimeric guide strand against murine coagulation Factor VII (miFVII, 5'-gta aga ctt gag a [none] 2o'ME[uga ucc]-(propyl)-3', antisense strand sequence from Akinc, et al. 2009 *Mol Ther* 17(5)872-879) were generated as described in Formula A except that chimeric guide strand was complexed in 63 μg of 10 kD polyornthine (Sigma) before dispersion and a modified LiCl salt receiving solution (135 mM $Li^+$, 9 mM $Ca^{2+}$, 14.06 nM $Sr^{2+}$, 6.25 nM $Mg^{2+}$ (all ultrapure)) was used for generating nanocapsules. Average particle size was 17.8±1.5 nm (mean±SE), and surface charge was −1±3.5 mev for the instant preparation.

Formula C:

sub-50 nm nanocapsules coated with ASOR and bearing a modified, double-stranded RNA oligonucleotide against murine ApoB (siApoB-1, sequence as described in Rozema, et al. 2007 *PNAS* 104(32):12982-87) were prepared as described in Formula A except that 25 mcg of ASOR was added to the hydrophobic micelles. When generating these nanocapsules, the ASOR-coated micelles were atomized into a modified LiCl salt receiving solution (135 mM $Li^+$, 9 mM $Ca^{2+}$, 26.3 nM $Sr^{2+}$, 15 nM $Mg^{2+}$ (all ultrapure)).

Formula D:

1000 μg of Dysprosium-chelated Dextran (from Example 1) was dispersed into 100 μl of sterile water using a water-insoluble surfactant system (2, 4, 7, 9-tetramethyl-5-decyn-4,7-diol (TM-diol; SE-30 (Air Products), 6.25 μg in 50% DMSO). Following emulsification with 150 μl of a water-miscible solvent (DMSO), the complexes were then inverted and diluted by the addition of 750 μl of PBS.

The resultant hydrophobic micelles were coated (non-covalently) by the addition of 50 μg of ASOR, then atomized into a modified LiCl salt receiving solution (135 mM $Li^+$, 9 mM $Ca^{2+}$, 27.5 nM $Sr^{2+}$, 13.75 nM $Mg^{2+}$ (all ultrapure)). Following cold-room incubation (4° C.) with nominal rotation in 50 ml round-bottomed tubes for 48 hours, which stabilizes the coated micelles in the salt solution, the sub-50 nm nanocapsules were recovered by centrifugal filtration with a Millipore Centricon-70 KD device and resuspended in PBS+10% lactitol for filter sterilization through a 0.2 μm filter. In all formulations described, a small amount (1% of coating weight) of Syrian Hamster Fab fragment was "spiked" into the ligand coat to enable immunodetection of nanocapsules uptake by anti-syrian hamster IgG antibodies. Average capsule size was between about 8-20 nm as measured by tapping mode atomic force microscopy using average of minor and major elliptical diameters of a 0.5 ng/ml sample dried down on a mica sheet. Formulations were subjected to one freeze-thaw before sizing analysis. Average zeta potential was between about +2 and −15 mev when measured on Zetasizer 4 dynamic light scattering device at a potential of 20 volts with a 2-second pause between measurements in 1 mM KCl at 2 μg/ml. Encapsulation yield for Dy content was determined by ICP.

Formula E:

sub-50 nm nanocapsules coated with TBG were generated as described in Formula A except that 31.25 mcg of recombinant fibrinogen fragment of tenascin (TBG; prepared by the modified method of Aukhill, et al. (1993 *J. Biol. Chem.* 268:2542-53) see below for method, precipitated in ultrapure 40% ammonium sulfate containing 250 ppb $As^{+3}$, 25 ppm $Se^{+4}$, 2.5 ppm $Hg^{+2}$ and 25 ppm $Mo^{+5}$ for about 16 hours) was added to 500 mcg of an antisense oligo to CK2 (phosphodiester 3' and propylendblocked—2OME RNA chimeric, "LCK-6", (PCT/US 2005/045820, incorporated herein by reference) and condensed with 125 mcg of 10 kD polyornthine (Sigma). When generating these nanocapsules, the Tbg-coated micelles were atomized into a modified LiCl salt receiving solution (135 mM $Li^+$, 9 mM $Ca^{2+}$, 7.5 nM Sr$^{2+}$, 2.3 nM Mg$^{2+}$ (all ultrapure, Sigma)) and capsules were incubated for 48 hours before centrifugation. Capsules were resuspended following centrifugation in PBS+10% Lactitol. Average capsule size was about 26.2± about 1 nm as measured by tapping mode atomic force microscopy using average of minor and major elliptical diameters of a 1 ng/ml sample dried down on a mica sheet and a surface charge of −8±4 mev was measured on Zetasizer 4 dynamic light scattering device at a potential of 20 volts with a 2-second pause between measurements in 1 mM KCl at 2 µg/ml.

The nanocapsules were administered in a pilot study to athymic nude mice bearing palpable flank xenograft tumors of FaDu hypopharangeal tumor. Growth inhibition at 24 hours after a third 10 µg/kg dose every third day was significant for tumors treated by a variety of treatment routes vs. controls (pooled treated vs. untreated 65% inhibition, 83±19 cu.cm vs. 236±33 cu. cm). Within the treatment group, growth inhibition was comparable or better to intravenous for subcutaneous via the back of the neck (tumor volume: (sq vs. iv): 92 vs. 126 cu. cm.; (topical by ear vs. i.v.): 36 vs. 126 cu. cm.), further supporting the view that s50 capsules can be administered subcutaneously with a variety of targeting ligands and cargo, and provide efficacious results.

Tenfibgen (TBG) Preparation:

TBG was prepared by the method of Aukhill with modifications, i.e., TBG was isolated and refolded from bacterial lysate by washing the insoluble pellet once with lysis buffer (50 mM Tris-HCl, 1.0 mM EDTA, 0.1 M NaCl, 0.2 mg/ml lysozyme, 0.1% Triton X-100, 0.1 mM PMSF, pH 8.0), containing 2 M urea and resuspending in 4M GuCL, 5 mM DTT in 0.02 M Tris-HCl, pH 8.0. After additional centrifugation, the clarified TBG solution was diluted with 2 M Guanidine-HCl, 20 mM Tris-HCl, pH 8.0 to make a final OD280 of about 1 and diluted dropwise about 10-fold into 20 mM Tris-HCl, 0.2 M NaCl, 0.5 M Arginine-HCl, 10 µM CuCl$_2$ pH 8.0 for overnight stirred incubation (4° C.). After diafiltration against 20 mM Tris-HCl, pH 8.0 with an approximate 4-5 fold reduction in concentration and 0.45 uM filtration, a final purification was performed on heparan sepharose in 20 mM Tris-HCl, pH 8.0, with elution by bringing the NaCl concentration to 0.6 M.

Formula F,

250 µg of 21 mer, Sistable™-modified, double-stranded RNA (Dharmacon) oligonucleotide (siFVII sequence, Akinc, et al. 2009 *Mol Ther* 17(5)872-879), was first complexed with 87.5 µg of 300 MW spermine (Sigma), then was dispersed into 100 µl of sterile water using a water-insoluble surfactant system (2, 4, 7, 9-tetramethyl-5-decyn-4,7-diol (TM-diol; SE-30 (Air Products), 6.25 µg in 50% DMSO). Following emulsification with 150 µl of a water-miscible solvent (DMSO), the complexes were then inverted and diluted by the addition of 750 µl of PBS.

The resultant hydrophobic micelles were coated (non-covalently) by the addition of 12.5 µg of asialoorosomucoid (ASOR; prepared by the method of Stockert, et al. (1980 *Lab. Invest.* 43:556-63)), then atomized into a modified LiCl salt receiving solution (135 mM Li$^+$, 9 mM Ca$^{2+}$, 14.1 nM Sr$^{2+}$, 11.25 nM Mg$^{2+}$ (all ultrapure, Sigma)). Following cold-room incubation (4° C.) with nominal rotation in 50 ml round-bottomed tubes for 48 hours, which stabilizes the coated micelles in the salt solution, the sub-50 nm nanocapsules were recovered by centrifugation at 20,000×g for 2 hrs and resuspended in PBS+10% lactitol (at a concentration of 0.5 µg/µl) for filter sterilization through a 0.2 µm filter. In all formulations described, a small amount (1% of coating weight) of Syrian Hamster Fab fragment was "spiked" into the ligand coat to enable immunodetection of nanocapsules uptake by anti-syrian hamster IgG antibodies. Average capsule size was about 20.2±0.6 nm as measured by tapping mode atomic force microscopy using average of minor and major elliptical diameters of a 1 ng/ml sample dried down on a mica sheet. Formulations were subjected to one freeze-thaw before sizing analysis. Average zeta potential was between about +2 and −15 mev (−3±4.5 mev) when measured on Zetasizer 4 dynamic light scattering device at a potential of 20 volts with a 2-second pause between measurements in 1 mM KCl at 2 µg/ml. Encapsulation yield was 100% by the modified method of Burton, Kren, et al. 200, *JCI* 119(7):2086-99.

Formula G,

500 µg of plasmid DNA was first complexed with 73 µg of 25 kDa polyethyleneimine (PEI; Sigma Chemical Co., St. Louis, Mo.), a branched cationic polymer, and dispersed into 150 µl of sterile water using a water-insoluble surfactant system (TM-diol; SE-30 (Air Products) in 50% DMSO). The DNA used in these experiments was a commercially available 4.5 kb reporter plasmid containing a Secreted Alkaline Phosphatase (SEAP) expression cassette (pCpg-marSEAP, Invivogen). Following emulsification with a water-miscible solvent (DMSO), the complexes were then inverted and diluted by the addition of 700 µl of PBS.

The resultant hydrophobic micelles were coated (non-covalently) by the addition of 25 µg of asialoorosomucoid (ASOR; prepared by the method of Stockert et al. (1980, *Lab. Invest.*, 43:556-63)) then atomized into a modified LiCl salt receiving solution (135 mM Li$^+$, 9 mM Ca$^{2+}$, 15 nM Sr$^{2+}$, 7.5 nM Mg$^{2+}$ (all ultrapure, Sigma)). Following cold-room incubation (4° C.) with nominal rotation in 50 ml round-bottomed tubes for 48 hours, which stabilizes the coated micelles in the salt solution, the sub-50 nm nanocapsules were recovered by centrifugation at 20,000×g for 2 hrs and resuspended in PBS+10% lactitol (at a concentration of 0.5 µg/µl) for filter sterilization through a 0.2 µm filter. In all formulations described, a small amount (1% of coating weight) of Syrian Hamster Fab fragment was "spiked" into the ligand coat to enable immunodetection of nanocapsules uptake by anti-syrian hamster IgG antibodies. Average capsule size was about 8.8±0.3 nm as measured by tapping mode atomic force microscopy using average of minor and major elliptical diameters of a 1 ng/ml sample dried down on a mica sheet. Formulations were subjected to one freeze-thaw cycle before sizing analysis. Zeta potential was between about +2 and −15 mev (−8±5 mev) when measured on Zetasizer 4 dynamic light scattering device at a potential of 20 volts with a 2-second pause between measurements in 1 mM KCl at 2 µg/ml. Encapsulation yield was 100% by the modified method of Burton, Kren, et al. 2009 *JCI* 119(7): 2086-99.

Formula H1,

250 µg of plasmid DNA (pVivo2-sahIRF7/3—LacZ, Invivogen) was first complexed with 38.7 µg of 25 kDa polyethyleneimine (PEI; Sigma Chemical Co., St. Louis, Mo.), a branched cationic polymer, and dispersed into 150 µl of sterile water using a water-insoluble surfactant system (TM-diol; SE-30 (Air Products), 7.5 µg in 50% DMSO). The DNA used in these experiments was a 10.5 kb commercially-available vaccine plasmid containing a LacZ expression cassette to produce betagalactosidase as a model antigen. Following emulsification with a water-miscible solvent (DMSO), the complexes were then inverted and diluted by the addition of 750 µl of PBS.

The resultant hydrophobic micelles were coated (non-covalently) by the addition of 6.3 µg of 22,480 Daltons hyaluronan (Sodium Hylarunonate Powder, GSP223-20, resuspended in water; Lifecore Biomedical); Formula H then was atomized into a LiCl salt receiving solution (135 mM Li+, 9 mM Ca2+, 1.25 nM Sr2+, 10.0 nM Mg2+ and 380 uM Ni2+ (all ultrapure)). Following cold-room incubation (4° C.) with nominal rotation for 14.5 hours in 50 ml round-bottomed tubes with the salt solution, which stabilizes the coated micelles, the sub-50 nm nanocapsules were recovered by centrifugation at 20,000×g for 2 hrs and resuspended in PBS+10% lactitol (at a concentration of 0.5 µg/µl) for filter sterilization through a 0.2 µm filter. In all formulations described, a small amount (1% of coating weight) of Syrian hamster Fab Fragment was "spiked" into the ligand coat to enable immunodetection of nanocapsules uptake by anti-syrian hamster IgG antibodies.

For formulas H2, H3, H4 and H5, the following substitutions from H1 were made. For H2 (LhaAl pVivo), 827 μM $AL^{3+}$ was substituted for nickel ion in the salt receiving solution in which 10 nM Sr2+, 27.5 $Mg^{2+}$ were used. For H3 (HaNi pVivo), 6.3 μg of 1 mM MW hyaluronan (Lifecore Biomedical) was substituted for low MW hyaluronan fragment with 1.75 nM $Sr^{2+}$ and 21 nM $Mg^{2+}$ (i.e., the quantities of $Sr^{2+}$ and $Mg^{2+}$ used for Formula H1 were changed to 1.75 nM and 21 nM, respectively, for Formula H2) in the receiving bath. For H4 (WJ6Ni pVivo), 6.3 μg of mouse anti-bovine Dec205 antibody (clone WJ6, MCA1651G, Serotec) was substituted for hyaluronan fragment as the coating ligand and capsule shell with 1.5 nM $Sr^{2+}$ and 27 nM $Mg^{2+}$ in the receiving bath. Dec205 is a surface receptor present on dendritic cell creating a nanoparticle targeting dendritic cells but not keratinocytes. For H5, a commercial betagal-expressing sequence (pcDNA3.1/LacZ, Invitrogen) based on the CMV promoter that was used in Formula H1, was condensed with 36.5 μg of 25 KD PEI, with 2 nM of $Mg^{2+}$+1.75 nM of $Sr^{2+}$ used in the receiver bath.

For all capsules, average capsule diameter was less than 50 nm as measured by tapping mode atomic force microscopy using elliptical diameters of a 0.5 ng/ml sample dried down on a mica sheet. Typical average capsule size was about 30-40 nm diameter. Zeta potential was between about +2 and −15 mev when measured on Zetasizer 4 dynamic light scattering device at a potential of 20 volts with a 2-second pause between measurements in 1 mM KCl at 2 μg/ml.

Example 3

Knockdown of FVII mRNA and Total Protein in Mice after Single Treatment with ASOR-Coated s50 Capsules Bearing RNAi Cargo In an effort to identify administrative routes more amenable than intravenous to chronic administration of nucleic acid and other pharmaceutical agents, C57B/6 mice of a minimum of 11 weeks were treated with bolus subcutaneous injection of s50 ASOR capsules bearing RNAi oligos in the back of the neck. In order to administer equal amounts of active agent, i.e., antisense guide strand, mice were treated with 10-25 nm s50 ASOR capsules bearing either 1 mg/kg siFVII (Formula A, example 2) or 0.5 mg/kg RNAi FVII, as single-stranded chimeric oligo displaying the antisense guide strand sequence for siFVII (Formula B, example 2).

Injection volumes were approximately 200 μl. Control formulations consisted of subcutaneous PBS (phosphate-buffered saline, 200 μl), intravenous 1 mg/kg s50 ASOR siApoB (Formula C, example 2) and subcutaneous s50 ASOR capsules bearing Dysprosium Dextran chelate, an experimental contrast agent @ 1 μg/kg or 300 nmol Dy/kg in 200 μl (~3× an imaging dose, Formulas D, example 2).

Animals were bled and euthanized in groups over a 5-day timecourse to follow the relationship between changes in coagulation FVII mRNA and protein levels. A significant 50% reduction in mRNA transcript (fold-HPRT, n=7-9) was measured at 48 hours post-treatment, the first timepoint (FIG. 1). This significant reduction in FVII liver mRNA preceded by 24 hours a significant 50% reduction in liver FVII total protein (by ELISA, n=6-8, FIG. 2) for double-stranded RNAi cargo and coincided for single-stranded RNAi cargo. The more rapid kinetics of change continued for single-stranded cargo with a significant nadir of plasma FVII protein knockdown of 93% on Day 3 and of 87% on Day 4 post-treatment for double-stranded RNAi cargo (n=6-8). As a comparison, mice treated intravenously with s50 ASOR capsules bearing double-stranded siFVII showed a significant 84% reduction in plasma FVII protein on Day 4 post-treatment (n=3), indicating comparable performance by subcutaneous and intravenous routes by the s50 capsule delivery carrier.

These effects were not attributable to the capsule delivery carrier itself, as mice treated with either the ASOR s50 capsules bearing a non-nucleic acid cargo (dysprosium) or with the s50 ASOR capsules bearing an irrelevant siRNA (siApoB, Example 2, Formula C), sacrificed over the course of the study, showed no significant change in FVII mRNA or protein levels (FIG. 1, 2). A third control s50 ASOR capsule, bearing an siRNA against a non-mammalian target, Red Fluorescent Protein, exhibited a pattern not unexpected with introducing siRNA against non-endogenous targets, in that a significant 30% knockdown in FVII liver mRNA was observed, coupled with non-significant inhibition of plasma and liver protein (2010 *Nucl Acids Res* 38 (1):1-16). Thus, the s50 capsule technology showed significant utility for subcutaneous delivery of charged macromolecules.

Plasma and liver protein levels were determined by a direct antibody ELISA using the manufacturer's recommended protocol (MAB 3305 clone 406722; R&D Systems, Mpls, Minn.). Liver mRNA levels of Factor VII were determined by qPCR using standard primers for mouse FVII and HPRT from SAB Biosciences per the manufacturer's recommended protocols and reagents (SAB Biosciences, Bethesda, Md.).

Example 4

Inhibition of Clotting Activity by s50 Encapsulated siFVII by Decreased Subcutaneous Dosing In an effort to further identify methodologies for reduced invasiveness in treatment administration of nucleic acids and other diagnostic and therapeutic cargos, dose response was investigated for anti-coagulation in female C57/B6 mice of at least 11 weeks, using an anti-FVII sequence (sistFVII, sequence same as Example 3, prepared as Formula F of example 2) with a stabilized backbone chemistry (Dharmacon, Lafayette, Co. sistable chemistry). Mice were treated with bolus subcutaneous injection of s50 ASOR capsules bearing siRNA oligos in the back of the neck. Injection volumes were approximately 200 μl. Control formulation consisted of subcutaneous PBS (phosphate-buffered saline, 200 μl).

Animals were bled and euthanized in groups after 3 days to follow the relationship between changes in coagulation and drug administration. Animals were treated in groups of three at the following doses; 2 mg/kg, 1 mg/kg, 0.5 mg/kg, 0.25 mg/kg and 0.1 mg/kg. Surprisingly, anti-clotting activity, as assessed by examination for clots in the lung and carcass, and the ability of blood to flow easily from a hematocrit collection tube after 10-15 minutes of rest, were present in all mice in the first four dosage groups as well as 2/3 of the mice in the lowest dose group, indicating a capacity for 4-10-fold or more dose reduction and an accompanying reduction in dose volume (and injection pain) by subcutaneous injection relative to our comparator dose from Example 3. For the 0.25 mg/kg group, active protein as measured by Factor VII activity ELISA was reduced (0.69±0.02 vs. control, n=3) corresponding to a parallel 25% reduction in mRNA transcript of 0.76±0.01 vs. control, n=3. Further significant utility was thus found for subcutaneous delivery of charged macromolecules via s50 capsules.

Example 5

Sub-50 nm Capsules Bearing Dysprosium-Dota-Dextran (DyDex) for Near IR(NIR) Imaging, Fluorescence Microscopy and Quantitative Neutron Activation Analysis (NAA)

Results herein demonstrate DyDex within the s50 capsule chemistry functions as a long-term, non-bleaching fluorescent probe in a water environment. This is highly surprising, as lanthanide luminescence, derived from electron mobility between outer F orbitals, is rapidly quenched by water contact. Relative to other water-quenched lanthanides, Dysprosium luminescence is considered the least stable with a time constant of only 9-11 μsec in aqueous media (Mudring, et al. 2006 *J Alloys Cmpd* 418:204-208), e.g., for lanthanide label series, fluorescent lifetimes were Tb(III), 695 us; Eu(III) 618 us; Sm(III) 89 us; Dy(III) not detectable (Huhtinen, et al. 2005 *Anal. Chem.* 77:2643-2648).

FIG. 3 shows excised organs (spleen, kidney, liver) from two mice, one of which (right hand side) was administered 1 μmol/kg (expressed as Dy amount) of s50 ASOR DyDex i.v. 30 hours before imaging (Formula D from Example 2). The other mouse (left-hand side) was not treated. Excised livers, kidneys, or spleen were imaged on at Kodak Carestream FX pro imaging station at 510 excitation and 700 nm emission with 20 nm bandpass filtering using a Kodak Carestream Multispectral imaging system with a xenon lamp light source. Results were processed with Kodak Multispectral imaging analysis software to extract Dy-specific signal and presented as grayscale (white as positive signal, for a pseudocolour scale (red-orange-yellow-white, 1750-2450 au), pseudocolor not shown. Specific Dy emission was observed as 50% of scale signal uniformly throughout two major liver lobes and minor lobe (depicted as medium white, identified with three narrow arrows or red-orange on a pseudocolor scale). A 75% scale signal was detected in the gall bladder (depicted as bright white with broad arrow or orange-yellow on a pseudocolor scale), indicating a higher accumulation in this organ consistent with hepatobilliary excretion of intact s50 ASOR capsule eventually into the feces. The spleen and kidney of the treated mouse, and the spleen, kidney, gall bladder, and liver of the untreated mouse were completely negative for signal (depicted as dark grey for grayscale or a green on a pseudocolor scale), establishing by s50 DyDex optimal imaging the liver-targeting capability of ASOR-targeted capsules administered intravenously.

The s50 nanoparticle chemistry together with Dy-chelated cargo provides the important advantage and benefit of facile preparation methods, incorporating proteins, peptides, antibodies, carbohydrates or small molecules as ligands in the shell. Ligands may be readily exchanged for diagnostic purposes in s50 ligand-targeted particles, e.g., tenfibgen or ASOR may be substituted for an anti-PSA antibody as a ligand to enable a diagnostic imaging agent or theranostic capable of identifying patient populations for treatment guidance.

The s50 capsule together with Dy-chelated cargo such as DyDex also provides high sensitivity in NAA (Dy detectable to 0.1 ppb). This physical characteristic derives in part from the large size of the Dy nucleus enabling it to function as a favorable target for neutron bombardment and activation. This feature enables measurement of Dy cargo as an isotopic tracer by quantitative method. For example, Table 1, below, shows quantitation of Dy metal in organs and fluids collected during a 24 hour period from mice injected by either intravenous, intraperitoneal, subcutaneous, or topical routes (one mouse each) with 250 nmol/kg (expressed as Dy amount) s50 ASOR DyDex. Fluids were collected using metabolism cages and tissue samples were carefully weighed before shipment to a nuclear reactor facility (Univ. Missouri) for neutron bombardment and gamma counting.

TABLE 1

| Organ accumulation | NAA measurement after 250 nmol/kg s50 ASOR DyDex @ 24 hours | | | |
|---|---|---|---|---|
| (% injected dose/g tissue) | intravenous | intraperitoneal | subcutaneous | passive topical by ear |
| Blood | 0.00 | 0.00 | 0 | 0 |
| Spleen | 3.14 | 0.00 | 0 | 0 |
| Liver | 38.50 | 3.10 | 1.39 | 0 |
| Lung | 0.83 | ND | ND | ND |
| Kidney | 0.52 | 0.00 | 0.10 | 0 |
| Jejunum | 0.16 | 0.00 | ND | ND |
| Urine | 16.61 | 4.15 | 1.58 | 1.3 |
| Feces | 7.54 | 11.64 | 23.8 | 61.3 |
| Injection site (tail) | 0.99 | ND | ND | ND |
| TOTAL IDENTIFIED | 68.29 | 18.89 | 26.87 | 62.60 |

Examination of the table shows that consistent with NIR imaging described in FIG. 3 where Dy signal was highest in the gall bladder, significant amounts of Dy were found in the feces relative to urine supporting hepatobiliary excretion. Subcutaneous delivery showed a small amount of Dy delivery to the target organ, liver. Topical delivery did not result in delivery to the liver but was as effective as intravenous in terms of delivering Dy across the skin barrier and into the body (iv vs. to; 68.29 vs. 62.60 ng Dy, Table 1). As the majority of topically-delivered Dy was found in the feces, this is consistent with direct delivery to the colon by lymphatics, however, it still demonstrates quantitatively very efficient transport of cargo by s50 nanoparticles across the skin.

It appears the ASOR ligands, when applied topically, is directed to the colon and feces, but topical work with another s50 ligand indicated desired organ (tumor) targeting was achieved (Example 2, Formula E, tenfibgen ligand). Additionally, the lower amount of DyDex measured for subcutaneous delivery in Table 1 (26.87) is consistent with the likely lymphatic transport of subcutaneously administered s50 ASOR particles (lymphatics were not assayed in this study; see also Example 4).

These data demonstrate the quantitative nature of Dy cargo as a tracer and suggest methods for bulk quantitation of target cells (e.g., tumor cells) in tissue by analytical methods (e.g., ICP-AES, NAA). Such bulk measurement would improve sensitivity of detection over spot sampling methods such as tissue sectioning and microscopic observation. Also advantageously, in line with the multi-modal nature of Dy detection, these bulk measurements can be readily correlated with current microscopy-based methods of detection due to the long-term retained fluorescence of Dy within the hydrophobic environment within the s50 capsule within formalin-fixed tissue. For example, the use of tumor-targeted capsules bearing fluorescent Dy cargo has been administered in tumor margin analysis post-resection.

Example 6

Subcutaneous Delivery of Plasmid DNA by s50 Nanocapsule

In an effort to identify feasible strategies for patient-friendly, chronic dosing in gene therapy protocols, two different regimens for subcutaneous (sq) administration and intravenous (iv) administration were compared. Outbred, immunocompetent mice (Swiss Webster, groups of three each) were treated with hepatocyte-targeting ASOR s50 capsules bearing the non-integrating reporter plasmid pCpg-freeSEAP (Formula G of Example 2) with the following regimens; 1) 3×10 mg/kg q3 Day intravenous, 2) 3×20 mg/kg q3 Day sq or 3) 6×10 mg/kg q3 Day sq. Comparator/control mice were treated with saline or 3×10 mg/kg q3 Day intravenous ASOR s50 capsules bearing trehalose sugar. Mice were sacrificed and livers collected for microscopy and RNA analysis two days after the last dose. For analysis of SEAP transcript, total RNA was isolated from ~50 mg of snap frozen liver tissue using the Qiagen RNeasy Lipid Tissue Mini Kit including the on column DNase digestion step according to the manufacturers protocol. RT-PCR was performed using the QIAGEN OneStep RT-PCR kit using forward primer and backward primer as disclosed in Example 6 of U.S. patent application Ser. No. 13/071,067, to amplify a 207 bp fragment of SEAP corresponding to nt 332 to 539 of the coding sequence (CDS).

The 50 µl reactions used 1 µg of total liver RNA as template, and the concentrations of all the other components including the Q buffer used were those specified by the manufacturer. The reverse transcriptase step was performed at 50° C. for 30 min, followed by a 15 min denaturation step at 95° C., followed by 35 cycles of (94° C. 45 sec, 56° C. 30 sec, 72° C. 1 min), followed by a 10 min extension step at 72° C. Band analysis was performed by electrophoresis of 20 µl of the reactions on 1.25% agarose gels and the material visualized using ethidium bromide and UVlight. Gels, depicted in FIG. 4A, indicate that 2/3 animals for each group of treated animals (intravenous and two subcutaneous protocols, Groups A and C) exhibited positive PCR bands for alkaline phosphatase transcript (6×10 mg/kg: 40% of iv, 3×20 mg/kg: 30% of iv by mean band density). No animals in the control groups (water and sugar s50) exhibited positive PCR bands for alkaline phosphatase transcript. Expression at the protein level was confirmed by microscopy (data not shown). These results are surprising, as repeat dosing has been highly problematic for plasmid delivery strategies, which have typically been based on particles larger than 50 nm in diameter and/or protein or carbohydrate targeting. For viral-based delivery strategies, antibodies against the vehicle/vector generally develop after one administration.

To study sq administration of s50 capsules independently of cargo transgene expression we used ASOR capsules carrying Dysprosium (Dy)-chelated dextran (Formula D of Example 2). Dy is a large nuclei, fluorescent lanthanide enabling sensitive isotopic measurements of tissues by neutron activation analysis of Dy content. A cohort of mice (5 groups, one mouse per group) were injected with 100 nmol/kg (expressed as Dy amount) sq over a 5 day period and held in metabolism cages for the final 24 hrs before sacrifice and tissue collection for Dysprosium content analysis. Over 5 days, ~4.3% of the injected dose accumulated in the liver (based on summation of 24-hr collection points for the 5 days) peaking at 3 days post-injection (see FIG. 5). In this analysis, 23% of the injected dose (summing all data points over the five day period) is accounted for. In other s50 studies (not shown), much of the non-organ distribution at late timepoints was found in the carcass (e.g., lymphatics); potentially, this would continue to distribute to the s50-targeted organ over a period of time as a depot effect.

Of note, no significant uptake was observed in spleen, kidney, lung, heart or testes (kidney data shown in FIG. 5, other data not shown), nor was there any evidence of injection site reaction from repeat injection. These data support the view that sq delivery of ASOR targeted s50 capsules to hepatocytes is specific and provides a depot effect, with prolonged availability of cargo and possible avoidance of duration-adverse effects such as saturation of cellular uptake, intracellular enzymatic degradation of cargo, etc.

Taken together, these results are very surprising, as targeted delivery of therapeutic plasmid DNA by subcutaneous delivery has not been demonstrated in vivo by non-viral or fully synthetic means and has not been believed to be possible due to the large size of the plasmid molecule.

Example 7

Enhanced Treatment Outcomes for s50 Capsule-Mediated DNA Vaccine Delivery in a Weanling Pig Model A 6 weanling pig pilot study was initiated comparing the immunostimulation from standard i.d. treatments (naked DNA expressing antigen or protein and protein antigen adjuvanted with incomplete Freund's) to candidate topical nanocapsule DNA vaccines directed against the model antigen β-galactosidase. The pilot study was designed to allow comparison of i) nickel vs. aluminum ion as adjuvant, ii) antigen vector designs, iii) the relative value of targeting keratinocytes+Langerhans cells/dendritic cells (LC/DC) vs. LC/DC alone and iv) specific antibody and cellular responses relative to standard i.d. inoculation of adjuvanted protein antigen and naked DNA. Preparation of important formulations is described in Example 2 under Formula H. A regimen of 3×500 µg DNA @ weeks 0.3, and 5 with termination at week 7 was used. Specific cellular targeting for either dendritic cells alone (Formula H4) or combination DC and keratinocyte was confirmed for capsule designs by transduction studies in pig biopsy skin organ culture.

After cleaning the skin with cloth and water, s50 hyaluronan capsules encapsulating DNA sequence for antigen and targeted to keratinocytes and DC (LHaNi, Formula H1) were sprayed on back of neck, thorax, and throat (500 µg DNA in 10 ml PBS plus 1 drop blue food coloring, equivalent to a dose of 0.44 µg/sq.cm based on treated surface area and approximately 10% of total body surface area, pig #866)), dosed at 3×500 µg (week 0, 3, 5). This formulation generated by ELISA specific IgG within about 1 log of the IgG level generated by i.d. protein antigen combined with incomplete Freund's adjuvant (3× at 500 μg, pig #864). Functional protein antigen production by DNA vaccine plasmid in skin was confirmed by polymerase chain reaction for Bgal transcript for Formula H1 (administered to pig #866, data not shown). No treatment site complications were observed at week 7 study termination in the topical delivery of nickel-adjuvant capsules bearing DNA, while complications including granuloma and redness and irritation were observed with the protein antigen i.d. treatment. s50 capsule IgG titer was two-fold that of naked i.d. DNA inoculation (3× at 500 μg, pig #863) and s50 capsules targeted to DC exclusively using anti-Dec205 binding (FIG. 6C) A second betagal-expressing vector was formulated (H5) in the optimal capsule design and produced a specific immune response (pig #865), demonstrating capability of the capsules to effectively deliver different antigenic loads.

Combined s50 targeting to keratinocytes and dendritic cells together with nickel adjuvant induced equivalent or better specific IgA responses as compared to standard i.d. inoculation of protein antigen (naked DNA from nasal lavage, demonstrating enhancement in mucosal humoral response (see FIG. 6B). Formula H1, s50 LhaNi, administered to pig #866, showed improved and more persistent mucosal IgA response over pig#867, treated with Formula H4, targeted at DC only. These results were particularly surprising, as the view in the art has been that keratinocyte cells are only weakly immunogenic and do not productively contribute to vaccine response, thus creating a weaker response for those vaccine formulations with any ancillary targeting to keratinocytes. Consistent with this observation, both the nanoparticle targeting dendritic cells, but not keratinocytes (Formula H4 of Example 2), and the low molecular weight hyaluronan utilizing aluminum ion as an adjuvant (Formula H2 of Example 2) showed no increase in IgA response vs. intradermal treatments.

Regional biasing of responses was suggested with i.d. inoculation showing strong splenic cellular responses but poorer nodal responses. In contrast, splenic cellular responses were completely absent following topical DNA nanocapsule application with statistically significant stronger nodal responses in both distal and draining lymph nodes over standard intradermal adjuvanted protein antigen (See FIG. 6A).

The candidate combo-targeted capsule design of LHaNi pVivo (administered to Pig #866, Formula H1 of Example 2) appeared to be optimal amongst the s50 capsule options tested. Specific IgA response was persistent and 2.5× naked i.d. DNA by grand average while specific lymphocyte response was 37× for draining nodacytes and 12.1× for distal nodacytes (p<0.05) over standard i.d. protein inoculation.

These results were surprising, as low molecular weight hyaluronan—nickel particles exhibited combination targeting to dendritic cells and keratinocytes relative to dendritic cells alone (DC targeting executed by Formula H4 of Example 2). Low molecular weight hyaluronan as a ligand relative to high MW (1 mM Da) hyaluronan was also surprising as an optimal ligand. Western blot analysis showed the low molecular weight treatment (LhaNi-pβgal, Formula H1, 5 μg plasmid DNA) induced twice as much betagal production in pigskin biopsy organ culture three days after treatment, as the high molecular weight treatment (high MW hyaluronan-Ni pβgal, Formula H3, 5 μg) (measured relative to lactate dehydrogenase, data not shown). LhaNi-pβgal treatment stimulated 1.6× more IL-1B cytokine than high MW hyaluronan-Ni pβgal (data not shown) into supernatants from pigskin biopsy organ culture three days after treatment. IL-1B is a cytokine associated with keratinocytes in the skin, and keratinocytes are believed in the art to be weakly immunogenic and not contributory to vaccine responses. Formula H4, the DC-targeting nanocapsule, did not stimulate any increased IL-1B into supernatants. Further, keratinocytes are surrounded by a glycocalyx of high MW hyaluronan and not known to respond to low molecular weight hyaluronan at all.

The results are likewise surprising, because they are produced in a large-animal model. Indeed, it is known in the art that, despite the success of non-viral DNA-based vaccines in small animal models, studies in large animals have not yielded similar success.

Example 8

Comparison of Factor VII (FVII) Activity Levels in Mice Treated with Oligonucleotides Via Subcutaneous and Intravenous Routes, with Nanoparticles of Different Size Studies were conducted in C57/B6 female mice to evaluate FVII activity levels for different routes and formulations of ASOR-coated sub-50 nanometer (s50) particles encapsulating siRNA cargo targeting FVII (siFVII). The siRNA medicinal chemistry included modifications for the 20 and 28 nm particle formulations, and no modifications for the 22 nm formulations (22 nm: Example 2, Formula A, 20 nm: Example 2, Formula F). A common siFVII sequence for all formulations was used as described in Akinc, et al. 2009 Mol Ther 17(5)872-879 for siFVII sense and siFVII antisense, as disclosed in U.S. patent application Ser. No. 13/071,067. Surface charge measured by zeta potential was equivalent between formulations, leaving particle size as the major statistical significant parameter different between formulations.

All mice were treated 1× at 1 mg/kg of body weight. FVII activity levels were determined by FVII activity ELISA (Biophen FVII; Aniara, Mason, Ohio) for the 20 and 28 nm particles, and by direct protein ELISA (MAB 3305 clone 406722; R&D Systems, Minneapolis, Minn.) for the 22 nm particles. FVII activity levels were measured on Days 2, 3, and 4 post-treatment for the mice treated subcutaneously (sq) with 20 and 28 nm particles, on Days 2, 3, 4, and 5 for mice treated sq with 22 nm particles, on Days 2 and 3 for mice treated i.v. with 20 nm and 28 nm particles, and on Day 4 for mice treated i.v. with 22 nm particles.

Table 2, below, shows nadir FVII activity levels for each formulation and route cohort. Only minor differences were found in FVII activity levels between sq and intravenous (i.v.) routes for the smallest (20 and 22 nm) particles, but substantial differences between routes for the largest (28 nm) particles.

TABLE 2

| s50 nanoparticles with siRNA cargo (diameter*, nm, mean ± SE) | s50 nanoparticles with siRNA cargo (surface charge**, mev, mean ± SE) | FVII plasma activity levels, vs. PBS control (% activity, measurement day, no. mice) | |
|---|---|---|---|
| | | Subcutaneous | Intravenous |
| 28 ± 0.6 nm, (n = 25) | −5 ± 3.8 | 74% ± 0 (D3, n = 2) | 19% ± 7 (D3, n = 2) |
| 22 ± 1 nm, (n = 10) | −5.5 ± 5.4 | 13% ± 2 (D4, n = 8) | 16% ± 5 (D4, n = 3) |

TABLE 2-continued

| s50 nanoparticles with siRNA cargo (diameter*, nm, mean ± SE) | s50 nanoparticles with siRNA cargo (surface charge**, mev, mean ± SE) | FVII plasma activity levels, vs. PBS control (% activity, measurement day, no. mice) | |
|---|---|---|---|
| | | Subcutaneous | Intravenous |
| 20 ± 0.6 nm, (n = 25) | −3 ± 4.5 | 32% ± 10 (D2, n = 4) | 37% ± 10 (D2, n = 5) |

*Particle diameter measured as average of major and minor elliptical axes by atomic force microscopy after drying of the suspension onto mica at 0.5 ng/ml or less of oligo.
**Zeta Potential measured by DLS across a 20 volt potential in 1 mM KCl at 2 μg/ml. of oligo.

The findings that i.v. formulations were observed to substantially inhibit FVII activity for all of the modified and unmodified cargoes indicates the s50 particle is compatible and effective with a range of oligo chemistries. Those observations, and the findings that the sq oligo formulations were most effective for the smallest particles (with modified and unmodified cargoes), show the diminished sq efficacy at 28 nm is attributable to particle size and not to oligo-related factors (e.g., intracellular nuclease resistance or target binding efficiency).

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

The invention claimed is:

1. A method of inducing an immune response in a non-rodent mammal, comprising topically administering to said non-rodent mammal an effective amount of a composition comprising non-viral nanoparticles comprising:
   (a) a micelle core comprising an antigen that is a DNA plasmid and a surfactant that has an HLB value of less than or equal to about 6.0,
   (b) a shell adsorbed to the micelle core and comprising a ligand, lithium, and an adjuvant, wherein the ligand comprises hyaluronan with an average molecular weight of between about 5,000 and 30,000 Daltons that is non-covalently attached to the nanoparticles, wherein the nanoparticles have a mean diameter of less than about 50 nanometers, wherein topically administering the composition stimulates a cytokine.

2. The method of claim 1, wherein the topically administered composition is applied to between about 0.001% and about 30% of the mammal's surface area.

3. The method of claim 1, wherein the composition is administered passive-topically.

4. The method of claim 1, wherein the composition is administered topically to an ear of said non-rodent mammal.

5. The method of claim 1, wherein the composition is administered to a mucosal surface of said non-rodent mammal.

6. The method of claim 1, wherein the induced immune response is antigen-specific.

7. The method of claim 1, wherein the administered composition targets keratinocyte cells.

8. The method of claim 1, wherein the administering is for prophylactic use.

9. The method of claim 1, wherein the administering is for therapeutic use.

10. The method of claim 9, where the therapeutic use is for treatment other than for tumor treatment.

11. The method of claim 1, wherein the cytokine is selected from the group consisting of interleukin-6 (IL-6), interleukin-10 (IL-10), interferon-alpha (IFN-α), and interleukin-1 beta (IL-1B).

12. The method of claim 11, wherein the cytokine is IL-1B.

* * * * *

SEQUENCE LISTING

<160> NUMBER OF SEQ ID NOS: 8

<210> SEQ ID NO 1
<211> LENGTH: 7616
<212> TYPE: DNA
<213> ORGANISM: Homo sapiens

<400> SEQUENCE: 1
attacagagg aaggagctcg ctatataagc cagccaaagt tggctgcacc ggccacagcc 60
tgcctactgt cacccgcctc tcccgcgcgc agatacacgc ccccgcctcc gtgggcacaa 120
aggcagcgct gctggggaac tcgggggaac gcgcacgtgg gaaccgccgc agctccacac 180
tccaggtact tcttccaagg acctaggtct ctcgcccatc ggaaagaaaa taattctttc 240
aagaagatca gggacaactg atttgaagtc tactctgtgc ttctaaatcc ccaattctgc 300
tgaaagtgag ataccctaga gccctagagc cccagcagca cccagccaaa cccacctcca 360
ccatgggggc catgactcag ctgttggcag gtgtctttct tgctttcctt gccctcgcta 420
ccgaaggtgg ggtcctcaag aaagtcatcc ggcacaagcg acagagtggg gtgaacgcca 480
ccctgccaga agagaaccag ccagtggtgt ttaaccacgt ttacaacatc aagctgccag 540
tgggatccca gtgttcggtg gatctggagt cagccagtgg ggagaaagac ctggcaccgc 600
cttcagagcc cagcgaaagc tttcaggagc acacagtgga tggggaaaac cagattgtct 660
tcacacatcg catcaacatc cccgcgcggg cctgtggctg tgccgcagcc cctgatgtta 720
aggagctgct gagcagactg gaggagctgg agaacctggt gtcttccctg agggagcaat 780
gtactgcagg agcaggctgc tgtctccagc ctgccacagg ccgcttggac accaggccct 840
tctgtagcgg tcggggcaac ttcagcactg aaggatgtgg ctgtgtctgc gaacctggct 900
ggaaaggccc caactgctct gagcccgaat gtccaggcaa ctgtcacctt cgaggccggt 960
gcattgatgg gcagtgcatc tgtgacgacg gcttcacggg cgaggactgc agccagctgg 1020
cttgccccag cgactgcaat gaccagggca agtgcgtaaa tggagtctgc atctgtttcg 1080
aaggctacgc cggggctgac tgcagccgtg aaatctgccc agtgccctgc agtgaggagc 1140
acggcacatg tgtagatggc ttgtgtgtgt gccacgatgg ctttgcaggc gatgactgca 1200
acaagcctct gtgtctcaac aattgctaca accgtggacg atgcgtggag aatgagtgcg 1260
tgtgtgatga gggtttcacg ggcgaagact gcagtgagct catctgcccc aatgactgct 1320
tcgaccgggg ccgctgcatc aatggcacct gctactgcga agaaggcttc acaggtgaag 1380
actgcgggaa acccacctgc ccacatgcct gccacaccca gggccggtgt gaggaggggc 1440

```
agtgtgtatg tgatgagggc tttgccggtg tggactgcag cgagaagagg tgtcctgctg    1500
actgtcacaa tcgtggccgc tgtgtagacg ggcggtgtga gtgtgatgat ggtttcactg    1560
gagctgactg tggggagctc aagtgtccca atggctgcag tggccatggc cgctgtgtca    1620
atgggcagtg tgtgtgtgat gagggctata ctggggagga ctgcagccag ctacggtgcc    1680
ccaatgactg tcacagtcgg ggccgctgtg tcgagggcaa atgtgtatgt gagcaaggct    1740
tcaagggcta tgactgcagt gacatgagct gccctaatga ctgtcaccag cacggccgct    1800
gtgtgaatgg catgtgtgtt tgtgatgacg gctacacagg ggaagactgc cgggatcgcc    1860
aatgccccag ggactgcagc aacagggccc tctgtgtgga cggacagtgc gtctgtgagg    1920
acggcttcac cggccctgac tgtgcagaac tctcctgtcc aaatgactgc catggccagg    1980
gtcgctgtgt gaatgggcag tgcgtgtgcc atgaaggatt tatgggcaaa gactgcaagg    2040
agcaaagatg tcccagtgac tgtcatggcc agggccgctg cgtggacggc cagtgcatct    2100
gccacgaggg cttcacaggc ctggactgtg ccagcactc ctgccccagt gactgcaaca    2160
acttaggaca atgcgtctcg ggccgctgca tctgcaacga gggctacagc ggagaagact    2220
gctcagaggt gtctcctccc aaagacctcg ttgtgacaga agtgacggaa gagacggtca    2280
acctggcctg gacaatgag atgcgggtca cagagtacct tgtcgtgtac acgcccaccc    2340
acgagggtgg tctggaaatg cagttccgtg tgcctgggga ccagacgtcc accatcatcc    2400
aggagctgga gcctggtgtg gagtacttta tccgtgtatt tgccatcctg gagaacaaga    2460
agagcattcc tgtcagcgcc agggtggcca cgtacttacc tgcacctgaa ggcctgaaat    2520
tcaagtccat caaggagaca tctgtggaag tggagtggga tcctctagac attgcttttg    2580
aaacctggga gatcatcttc cggaatatga ataagaaga tgaggagag atcaccaaaa    2640 gcctgaggag gccagagacc tcttaccggc aaactggtct agctcctggg caagagtatg    2700
agatatctct gcacatagtg aaaaacaata cccggggccc tggcctgaag agggtgacca    2760
ccacacgctt ggatgccccc agccagatcg aggtgaaaga tgtcacagac accactgcct    2820
tgatcacctg gttcaagccc ctggctgaga tcgatggcat tgagctgacc tacggcatca    2880
aagacgtgcc aggagaccgt accaccatcg atctcacaga ggacgagaac cagtactcca    2940
tcgggaacct gaagcctgac actgagtacg aggtgtccct catctcccgc agaggtgaca    3000
tgtcaagcaa cccagccaaa gagaccttca acacaggcct cgatgctccc aggaatcttc    3060
gacgtgtttc ccagacagat aacagcatca ccctggaatg gaggaatggc aaggcagcta    3120
ttgacagtta cagaattaag tatgccccca tctctggagg ggaccacgct gaggttgatg    3180
ttccaaagag ccaacaagcc acaaccaaaa ccacactcac aggtctgagg ccgggaactg    3240
aatatgggat tggagtttct gctgtgaagg aagacaagga gagcaatcca gcgaccatca    3300
acgcagccac agagttggac acgcccaagg accttcaggt ttctgaaact gcagagacca    3360
gcctgaccct gctctggaag acaccgttgg ccaaatttga ccgctaccgc tcaattaca    3420 gtctccccac aggccagtgg gtgggagtgc agcttccaag aaacaccact tcctatgtcc    3480
tgagaggcct ggaaccagga caggagtaca atgtcctcct gacagccgag aaaggcagac    3540
acaagagcaa gcccgcacgt gtgaaggcat ccactgaaca agcccctgag ctggaaaacc    3600
tcaccgtgac tgaggttggc tgggatggcc tcagactcaa ctggaccgca gctgaccagg    3660
cctatgagca ctttatcatt caggtgcagg aggccaacaa ggtggaggca gctcggaacc    3720
tcaccgtgcc tggcagcctt cgggctgtgg acataccggg cctcaaggct gctacgcctt    3780
```

-continued

```
atacagtctc catctatggg gtgatccagg gctatagaac accagtgctc tctgctgagg    3840
cctccacagg ggaaactccc aatttgggag aggtcgtggt ggccgaggtg ggctgggatg    3900
ccctcaaact caactggact gctccagaag gggcctatga gtacttttc attcaggtgc     3960
aggaggctga cacagtagag gcagcccaga acctcaccgt cccaggagga ctgaggtcca    4020
cagacctgcc tgggctcaaa gcagccactc attataccat caccatccgc ggggtcactc    4080
aggacttcag cacaaccccct ctctctgttg aagtcttgac agaggaggtt ccagatatgg   4140
gaaacctcac agtgaccgag gttagctggg atgctctcag actgaactgg accacgccag    4200
atggaaccta tgaccagttt actattcagg tccaggaggc tgaccaggtg gaagaggctc    4260
acaatctcac ggttcctggc agcctgcgtt ccatggaaat cccaggcctc agggctggca    4320
ctccttacac agtcaccctg cacggcgagg tcagggggcca cagcactcga cccccttgctg 4380
tagaggtcgt cacagaggat ctcccacagc tgggagattt agccgtgtct gaggttggct    4440
gggatggcct cagactcaac tggaccgcag ctgacaatgc ctatgagcac tttgtcattc    4500
aggtgcagga ggtcaacaaa gtggaggcag cccagaacct cacgttgcct ggcagcctca    4560
gggctgtgga catcccgggc ctcgaggctg ccacgcctta tagtctccc atctatgggg     4620
tgatccgggg ctatagaaca ccagtactct ctgctgaggc ctccacagcc aaagaacctg    4680
aaattggaaa cttaaatgtt tctgacataa ctcccgagag cttcaatctc tcctggatgg    4740
ctaccgatgg gatcttcgag accttttacca ttgaaattat tgattccaat aggttgctgg   4800
agactgtgga atataatatc tctggtgctg aacgaactgc ccatatctca gggctacccc    4860
ctagtactga tttattgtc tacctctctg gacttgctcc cagcatccgg accaaaacca     4920
tcagtgccac agccacgaca gaggccctgc cccttctgga aaacctaacc atttccgaca    4980
ttaatcccta cggggttcaca gtttcctgga tggcatcgga gaatgccttt gacagctttc   5040
tagtaacggt ggtggattct gggaagctgc tggacccccca ggaattcaca ctttcaggaa   5100
cccagaggaa gctggagctt agaggcctca taactggcat tggctatgag gttatggtct    5160
ctggcttcac ccaagggcat caaaccaagc ccttgagggc tgagattgtt acagaagccg    5220
aaccggaagt tgacaacctt ctggttcag atgccaccc agacggtttc cgtctgtcct       5280
ggacagctga tgaaggggtc ttcgacaatt ttgttctcaa aatcagagat accaaaaagc    5340
agtctgagcc actggaaata accctacttg cccccgaacg taccagggac ataacaggtc    5400
tcagagaggc tactgaatac gaaattgaac tctatggaat aagcaaagga aggcgatccc    5460
agacagtcag tgctatagca acaacagcca tgggctcccc aaaggaagtc attttctcag    5520
acatcactga aaattcggct actgtcagct ggaggcacc cacagcccaa gtggagagct     5580
tccggattac ctatgtgccc attacaggag gtacaccctc catggtaact gtggacggaa    5640
ccaagactca gaccaggctg gtgaaactca tacctggcgt ggagtacctt gtcagcatca    5700
tcgccatgaa gggctttgag gaaagtgaac ctgtctcagg gtcattcacc acagctctgg    5760
atggcccatc tggcctggtg acagccaaca tcactgactc agaagccttg gccaggtggc    5820
agccagccat tgccactgtg gacagttatg tcatctccta cacaggcgag aaagtgccag    5880
aaattacacg cacggtgtcc gggaacacag tggagtatgc tctgaccgac ctcgagcctg    5940
ccacggaata cacactgaga atctttgcag agaaagggcc ccagaagagc tcaaccatca    6000
ctgccaagtt cacaacagac ctcgattctc caagagactt gactgctact gaggttcagt    6060
cggaaactgc cctccttacc tggcgacccc ccgggcatc agtcaccggt tacctgctgg      6120
tctatgaatc agtggatggc acagtcaagg aagtcattgt gggtccagat accacctcct    6180
```

| | |
|---|---|
| acagcctggc agacctgagc ccatccaccc actacacagc caagatccag gcactcaatg | 6240 |
| ggccnctgag gagcaatatg atccagacca tcttcaccac aattggactc ctgtacccct | 6300 |
| tccccaagga ctgctcccaa gcaatgctga atggagacac gacctctggc ctctacacca | 6360 |
| tttatctgaa tggtgataag gctgaggcgc tggaagtctt ctgtgacatg acctctgatg | 6420 |
| ggggtggatg gattgtgttc ctgagacgca aaaacggacg cgagaacttc taccaaaact | 6480 |
| ggaaggcata tgctgctgga tttggggacc gcagagaaga attctggctt gggctggaca | 6540 |
| acctgaacaa aatcacagcc caggggcagt acgagctccg ggtggacctg cgggaccatg | 6600 |
| gggagacagc ctttgctgtc tatgacaagt tcagcgtggg agatgccaag actcgctaca | 6660 |
| agctgaaggt ggaggggtac agtgggacag caggtgactc catggcctac acaatggca | 6720 |
| gatccttctc cacctttgac aaggacacag attcagccat caccaactgt gctctgtcct | 6780 |
| acaaaggggc tttctggtac aggaactgtc accgtgtcaa cctgatgggg agatatgggg | 6840 |
| acaataacca cagtcagggc gttaactggt tccactggaa gggccacgaa cactcaatcc | 6900 |
| agtttgctga tgaagctg agaccaagca acttcagaaa tcttgaaggc aggcgcaaac | 6960 |
| gggcataaat tccagggacc actgggtgag agaggaataa ggcccagagc gaggaaagga | 7020 |
| ttttaccaaa gcatcaatac aaccagccca accatcggtc cacacctggg catttggtga | 7080 |
| gagtcaaagc tgaccatgga tccctggggc caacggcaac agcatgggcc tcacctcctc | 7140 |
| tgtgatttct ttctttgcac caaagacatc agtctccaac atgtttctgt tttgttgttt | 7200 |
| gattcagcaa aaatctccca gtgacaacat cgcaatagtt ttttacttct cttaggtggc | 7260 |
| tctgggaatg ggagaggggt aggatgtaca ggggtagttt gttttagaac cagccgtatt | 7320 |
| ttacatgaag ctgtataatt aattgtcatt attttgtta gcaaagatta aatgtgtcat | 7380 |
| tggaagccat ccctttttt acatttcata caacagaaac cagaaaagca atactgtttc | 7440 |
| catttaagg atatgattaa tattattaat ataataatga tgatgatgat gatgaaaact | 7500 |
| aaggattttt caagagatct ttctttccaa aacatttctg gacagtacct gattgtattt | 7560 |
| ttttttaaa taaagcaca agtacttttg agtttgttaa aaaaaaaaaa aaaaaa | 7616 |

<210> SEQ ID NO 2
<211> LENGTH: 2201
<212> TYPE: PRT
<213> ORGANISM: Homo sapiens

<400> SEQUENCE: 2

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
                20                  25                  30

Arg Gln Ser Gly Val Asn Ala Thr Leu Pro Glu Glu Asn Gln Pro Val
            35                  40                  45

Val Phe Asn His Val Tyr Asn Ile Lys Leu Pro Val Gly Ser Gln Cys
        50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu

```
            115                 120                 125
Leu Glu Asn Leu Val Ser Ser Leu Arg Glu Gln Cys Thr Ala Gly Ala
            130                 135                 140
Gly Cys Cys Leu Gln Pro Ala Thr Gly Arg Leu Asp Thr Arg Pro Phe
145                 150                 155                 160
Cys Ser Gly Arg Gly Asn Phe Ser Thr Glu Gly Cys Gly Cys Val Cys
                165                 170                 175
Glu Pro Gly Trp Lys Gly Pro Asn Cys Ser Glu Pro Glu Cys Pro Gly
                180                 185                 190
Asn Cys His Leu Arg Gly Arg Cys Ile Asp Gly Gln Cys Ile Cys Asp
                195                 200                 205
Asp Gly Phe Thr Gly Glu Asp Cys Ser Gln Leu Ala Cys Pro Ser Asp
            210                 215                 220
Cys Asn Asp Gln Gly Lys Cys Val Asn Gly Val Cys Ile Cys Phe Glu
225                 230                 235                 240
Gly Tyr Ala Gly Ala Asp Cys Ser Arg Glu Ile Cys Pro Val Pro Cys
                245                 250                 255
Ser Glu Glu His Gly Thr Cys Val Asp Gly Leu Cys Val Cys His Asp
                260                 265                 270
Gly Phe Ala Gly Asp Asp Cys Asn Lys Pro Leu Cys Leu Asn Asn Cys
            275                 280                 285
Tyr Asn Arg Gly Arg Cys Val Glu Asn Glu Cys Val Cys Asp Glu Gly
            290                 295                 300
Phe Thr Gly Glu Asp Cys Ser Glu Leu Ile Cys Pro Asn Asp Cys Phe
305                 310                 315                 320
Asp Arg Gly Arg Cys Ile Asn Gly Thr Cys Tyr Cys Glu Glu Gly Phe
                325                 330                 335
Thr Gly Glu Asp Cys Gly Lys Pro Thr Cys Pro His Ala Cys His Thr
                340                 345                 350
Gln Gly Arg Cys Glu Glu Gly Gln Cys Val Cys Asp Glu Gly Phe Ala
            355                 360                 365
Gly Val Asp Cys Ser Glu Lys Arg Cys Pro Ala Asp Cys His Asn Arg
            370                 375                 380
Gly Arg Cys Val Asp Gly Arg Cys Glu Cys Asp Asp Gly Phe Thr Gly
385                 390                 395                 400
Ala Asp Cys Gly Glu Leu Lys Cys Pro Asn Gly Cys Ser Gly His Gly
                405                 410                 415
Arg Cys Val Asn Gly Gln Cys Val Cys Asp Glu Gly Tyr Thr Gly Glu
                420                 425                 430
Asp Cys Ser Gln Leu Arg Cys Pro Asn Asp Cys His Ser Arg Gly Arg
            435                 440                 445
Cys Val Glu Gly Lys Cys Val Cys Glu Gln Gly Phe Lys Gly Tyr Asp
            450                 455                 460
Cys Ser Asp Met Ser Cys Pro Asn Asp Cys His Gln His Gly Arg Cys
465                 470                 475                 480
Val Asn Gly Met Cys Val Cys Asp Asp Gly Tyr Thr Gly Glu Asp Cys
                485                 490                 495
Arg Asp Arg Gln Cys Pro Arg Asp Cys Ser Asn Arg Gly Leu Cys Val
                500                 505                 510
Asp Gly Gln Cys Val Cys Glu Asp Gly Phe Thr Gly Pro Asp Cys Ala
            515                 520                 525
Glu Leu Ser Cys Pro Asn Asp Cys His Gly Gln Gly Arg Cys Val Asn
            530                 535                 540
```

-continued

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
                565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
        595                 600                 605

Cys Ile Cys Asn Glu Gly Tyr Ser Gly Glu Asp Cys Ser Glu Val Ser
610                 615                 620

Pro Pro Lys Asp Leu Val Val Thr Glu Val Thr Glu Thr Val Asn
625                 630                 635                 640

Leu Ala Trp Asp Asn Glu Met Arg Val Thr Glu Tyr Leu Val Val Tyr
                645                 650                 655

Thr Pro Thr His Glu Gly Gly Leu Glu Met Gln Phe Arg Val Pro Gly
            660                 665                 670

Asp Gln Thr Ser Thr Ile Ile Gln Glu Leu Glu Pro Gly Val Glu Tyr
        675                 680                 685

Phe Ile Arg Val Phe Ala Ile Leu Glu Asn Lys Lys Ser Ile Pro Val
690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Glu Thr Ser Tyr
        755                 760                 765

Arg Gln Thr Gly Leu Ala Pro Gly Gln Glu Tyr Glu Ile Ser Leu His
    770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
        835                 840                 845

Ile Asp Leu Thr Glu Asp Glu Asn Gln Tyr Ser Ile Gly Asn Leu Lys
    850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                885                 890                 895

Arg Asn Leu Arg Arg Val Ser Gln Thr Asp Asn Ser Ile Thr Leu Glu
            900                 905                 910

Trp Arg Asn Gly Lys Ala Ala Ile Asp Ser Tyr Arg Ile Lys Tyr Ala
        915                 920                 925

Pro Ile Ser Gly Gly Asp His Ala Glu Val Asp Val Pro Lys Ser Gln
    930                 935                 940

Gln Ala Thr Thr Lys Thr Thr Leu Thr Gly Leu Arg Pro Gly Thr Glu
945                 950                 955                 960

-continued

Tyr Gly Ile Gly Val Ser Ala Val Lys Glu Asp Lys Glu Ser Asn Pro
            965                 970                 975

Ala Thr Ile Asn Ala Ala Thr Glu Leu Asp Thr Pro Lys Asp Leu Gln
            980                 985                 990

Val Ser Glu Thr Ala Glu Thr Ser Leu Thr Leu Leu Trp Lys Thr Pro
        995                 1000                1005

Leu Ala Lys Phe Asp Arg Tyr Arg Leu Asn Tyr Ser Leu Pro Thr
    1010                1015                1020

Gly Gln Trp Val Gly Val Gln Leu Pro Arg Asn Thr Thr Ser Tyr
    1025                1030                1035

Val Leu Arg Gly Leu Glu Pro Gly Gln Glu Tyr Asn Val Leu Leu
    1040                1045                1050

Thr Ala Glu Lys Gly Arg His Lys Ser Lys Pro Ala Arg Val Lys
    1055                1060                1065

Ala Ser Thr Glu Gln Ala Pro Glu Leu Glu Asn Leu Thr Val Thr
    1070                1075                1080

Glu Val Gly Trp Asp Gly Leu Arg Leu Asn Trp Thr Ala Ala Asp
    1085                1090                1095

Gln Ala Tyr Glu His Phe Ile Ile Gln Val Gln Glu Ala Asn Lys
    1100                1105                1110

Val Glu Ala Ala Arg Asn Leu Thr Val Pro Gly Ser Leu Arg Ala
    1115                1120                1125

Val Asp Ile Pro Gly Leu Lys Ala Ala Thr Pro Tyr Thr Val Ser
    1130                1135                1140

Ile Tyr Gly Val Ile Gln Gly Tyr Arg Thr Pro Val Leu Ser Ala
    1145                1150                1155

Glu Ala Ser Thr Gly Glu Thr Pro Asn Leu Gly Glu Val Val Val
    1160                1165                1170

Ala Glu Val Gly Trp Asp Ala Leu Lys Leu Asn Trp Thr Ala Pro
    1175                1180                1185

Glu Gly Ala Tyr Glu Tyr Phe Phe Ile Gln Val Gln Glu Ala Asp
    1190                1195                1200

Thr Val Glu Ala Ala Gln Asn Leu Thr Val Pro Gly Gly Leu Arg
    1205                1210                1215

Ser Thr Asp Leu Pro Gly Leu Lys Ala Ala Thr His Tyr Thr Ile
    1220                1225                1230

Thr Ile Arg Gly Val Thr Gln Asp Phe Ser Thr Thr Pro Leu Ser
    1235                1240                1245

Val Glu Val Leu Thr Glu Glu Val Pro Asp Met Gly Asn Leu Thr
    1250                1255                1260

Val Thr Glu Val Ser Trp Asp Ala Leu Arg Leu Asn Trp Thr Thr
    1265                1270                1275

Pro Asp Gly Thr Tyr Asp Gln Phe Thr Ile Gln Val Gln Glu Ala
    1280                1285                1290

Asp Gln Val Glu Glu Ala His Asn Leu Thr Val Pro Gly Ser Leu
    1295                1300                1305

Arg Ser Met Glu Ile Pro Gly Leu Arg Ala Gly Thr Pro Tyr Thr
    1310                1315                1320

Val Thr Leu His Gly Glu Val Arg Gly His Ser Thr Arg Pro Leu
    1325                1330                1335

Ala Val Glu Val Val Thr Glu Asp Leu Pro Gln Leu Gly Asp Leu
    1340                1345                1350

Ala Val Ser Glu Val Gly Trp Asp Gly Leu Arg Leu Asn Trp Thr

-continued

```
                1355                1360                1365

Ala Ala Asp Asn Ala Tyr Glu His Phe Val Ile Gln Val Gln Glu
            1370                1375                1380

Val Asn Lys Val Glu Ala Ala Gln Asn Leu Thr Leu Pro Gly Ser
        1385                1390                1395

Leu Arg Ala Val Asp Ile Pro Gly Leu Glu Ala Ala Thr Pro Tyr
    1400                1405                1410

Arg Val Ser Ile Tyr Gly Val Ile Arg Gly Tyr Arg Thr Pro Val
1415                1420                1425

Leu Ser Ala Glu Ala Ser Thr Ala Lys Glu Pro Glu Ile Gly Asn
        1430                1435                1440

Leu Asn Val Ser Asp Ile Thr Pro Glu Ser Phe Asn Leu Ser Trp
    1445                1450                1455

Met Ala Thr Asp Gly Ile Phe Glu Thr Phe Thr Ile Glu Ile Ile
1460                1465                1470

Asp Ser Asn Arg Leu Leu Glu Thr Val Glu Tyr Asn Ile Ser Gly
        1475                1480                1485

Ala Glu Arg Thr Ala His Ile Ser Gly Leu Pro Pro Ser Thr Asp
    1490                1495                1500

Phe Ile Val Tyr Leu Ser Gly Leu Ala Pro Ser Ile Arg Thr Lys
1505                1510                1515

Thr Ile Ser Ala Thr Ala Thr Thr Glu Ala Leu Pro Leu Leu Glu
        1520                1525                1530

Asn Leu Thr Ile Ser Asp Ile Asn Pro Tyr Gly Phe Thr Val Ser
    1535                1540                1545

Trp Met Ala Ser Glu Asn Ala Phe Asp Ser Phe Leu Val Thr Val
1550                1555                1560

Val Asp Ser Gly Lys Leu Leu Asp Pro Gln Glu Phe Thr Leu Ser
        1565                1570                1575

Gly Thr Gln Arg Lys Leu Glu Leu Arg Gly Leu Ile Thr Gly Ile
    1580                1585                1590

Gly Tyr Glu Val Met Val Ser Gly Phe Thr Gln Gly His Gln Thr
1595                1600                1605

Lys Pro Leu Arg Ala Glu Ile Val Thr Glu Ala Glu Pro Glu Val
        1610                1615                1620

Asp Asn Leu Leu Val Ser Asp Ala Thr Pro Asp Gly Phe Arg Leu
    1625                1630                1635

Ser Trp Thr Ala Asp Glu Gly Val Phe Asp Asn Phe Val Leu Lys
1640                1645                1650

Ile Arg Asp Thr Lys Lys Gln Ser Glu Pro Leu Glu Ile Thr Leu
        1655                1660                1665

Leu Ala Pro Glu Arg Thr Arg Asp Ile Thr Gly Leu Arg Glu Ala
    1670                1675                1680

Thr Glu Tyr Glu Ile Glu Leu Tyr Gly Ile Ser Lys Gly Arg Arg
1685                1690                1695

Ser Gln Thr Val Ser Ala Ile Ala Thr Thr Ala Met Gly Ser Pro
        1700                1705                1710

Lys Glu Val Ile Phe Ser Asp Ile Thr Glu Asn Ser Ala Thr Val
    1715                1720                1725

Ser Trp Arg Ala Pro Thr Ala Gln Val Glu Ser Phe Arg Ile Thr
1730                1735                1740

Tyr Val Pro Ile Thr Gly Gly Thr Pro Ser Met Val Thr Val Asp
        1745                1750                1755
```

-continued

Gly Thr Lys Thr Gln Thr Arg Leu Val Lys Leu Ile Pro Gly Val
1760                1765                1770

Glu Tyr Leu Val Ser Ile Ile Ala Met Lys Gly Phe Glu Glu Ser
1775                1780                1785

Glu Pro Val Ser Gly Ser Phe Thr Thr Ala Leu Asp Gly Pro Ser
1790                1795                1800

Gly Leu Val Thr Ala Asn Ile Thr Asp Ser Glu Ala Leu Ala Arg
1805                1810                1815

Trp Gln Pro Ala Ile Ala Thr Val Asp Ser Tyr Val Ile Ser Tyr
1820                1825                1830

Thr Gly Glu Lys Val Pro Glu Ile Thr Arg Thr Val Ser Gly Asn
1835                1840                1845

Thr Val Glu Tyr Ala Leu Thr Asp Leu Glu Pro Ala Thr Glu Tyr
1850                1855                1860

Thr Leu Arg Ile Phe Ala Glu Lys Gly Pro Gln Lys Ser Ser Thr
1865                1870                1875

Ile Thr Ala Lys Phe Thr Thr Asp Leu Asp Ser Pro Arg Asp Leu
1880                1885                1890

Thr Ala Thr Glu Val Gln Ser Glu Thr Ala Leu Leu Thr Trp Arg
1895                1900                1905

Pro Pro Arg Ala Ser Val Thr Gly Tyr Leu Leu Val Tyr Glu Ser
1910                1915                1920

Val Asp Gly Thr Val Lys Glu Val Ile Val Gly Pro Asp Thr Thr
1925                1930                1935

Ser Tyr Ser Leu Ala Asp Leu Ser Pro Ser Thr His Tyr Thr Ala
1940                1945                1950

Lys Ile Gln Ala Leu Asn Gly Pro Leu Arg Ser Asn Met Ile Gln
1955                1960                1965

Thr Ile Phe Thr Thr Ile Gly Leu Leu Tyr Pro Phe Pro Lys Asp
1970                1975                1980

Cys Ser Gln Ala Met Leu Asn Gly Asp Thr Thr Ser Gly Leu Tyr
1985                1990                1995

Thr Ile Tyr Leu Asn Gly Asp Lys Ala Glu Ala Leu Glu Val Phe
2000                2005                2010

Cys Asp Met Thr Ser Asp Gly Gly Gly Trp Ile Val Phe Leu Arg
2015                2020                2025

Arg Lys Asn Gly Arg Glu Asn Phe Tyr Gln Asn Trp Lys Ala Tyr
2030                2035                2040

Ala Ala Gly Phe Gly Asp Arg Arg Glu Glu Phe Trp Leu Gly Leu
2045                2050                2055

Asp Asn Leu Asn Lys Ile Thr Ala Gln Gly Gln Tyr Glu Leu Arg
2060                2065                2070

Val Asp Leu Arg Asp His Gly Glu Thr Ala Phe Ala Val Tyr Asp
2075                2080                2085

Lys Phe Ser Val Gly Asp Ala Lys Thr Arg Tyr Lys Leu Lys Val
2090                2095                2100

Glu Gly Tyr Ser Gly Thr Ala Gly Asp Ser Met Ala Tyr His Asn
2105                2110                2115

Gly Arg Ser Phe Ser Thr Phe Asp Lys Asp Thr Asp Ser Ala Ile
2120                2125                2130

Thr Asn Cys Ala Leu Ser Tyr Lys Gly Ala Phe Trp Tyr Arg Asn
2135                2140                2145

```
Cys His Arg Val Asn Leu Met Gly Arg Tyr Gly Asp Asn Asn His
    2150                2155                2160

Ser Gln Gly Val Asn Trp Phe His Trp Lys Gly His Glu His Ser
    2165                2170                2175

Ile Gln Phe Ala Glu Met Lys Leu Arg Pro Ser Asn Phe Arg Asn
    2180                2185                2190

Leu Glu Gly Arg Arg Lys Arg Ala
    2195                2200

<210> SEQ ID NO 3
<211> LENGTH: 687
<212> TYPE: DNA
<213> ORGANISM: Homo sapiens

<400> SEQUENCE: 3
attggactcc tgtacccctt ccccaaggac tgctcccaag caatgctgaa tggagacacg    60
acctctggcc tctacaccat ttatctgaat ggtgataagg ctcaggcgct ggaagtcttc    120
tgtgacatga cctctgatgg gggtggatgg attgtgttcc tgagacgcaa aaacggacgc    180
gagaacttct accaaaactg gaaggcatat gctgctggat ttggggaccg cagagaagaa    240
ttctggcttg gctggacaa cctgaacaaa atcacagccc aggggcagta cgagctccgg    300
gtggacctgc ggaccatgg ggagacagcc tttgctgtct atgacaagtt cagcgtggga    360
gatgccaaga ctcgctacaa gctgaaggtg gaggggtaca gtggacagc aggtgactcc    420 atggcctacc acaatggcag atccttctcc acctttgaca ggacacaga ttcagccatc    480 accaactgtg ctctgtccta caagggggct ttctggtaca ggaactgtca ccgtgtcaac    540
ctgatgggga gatatgggga caataaccac agtcagggcg ttaactggtt ccactggaag    600
ggccacgaac actcaatcca gtttgctgag atgaagctga gaccaagcaa cttcagaaat    660
cttgaaggca ggcgcaaacg ggcataa                                        687

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined Molecule: Synthetic
      oligonucleotide

<400> SEQUENCE: 4
gtaagacttg agaugaucc                                                 19

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgggacaggc acagcattct tg                                             22

<210> SEQ ID NO 6
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 6
tgggcataag ttccagcagg ag                                              22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined Molecule: Synthetic
      oligonucleotide

<400> SEQUENCE: 7
ggaucaucuc aagucuuact t                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined Molecule: Synthetic
      oligonucleotide

<400> SEQUENCE: 8
guaagacuug agaugaucct t                                               21
```